US008124655B2

(12) United States Patent
Rahbar et al.

(10) Patent No.: US 8,124,655 B2
(45) Date of Patent: Feb. 28, 2012

(54) USE OF LR-90 AND LR-102 TO OVERCOME INSULIN RESISTANCE

(75) Inventors: Samuel Rahbar, Beverly Hills, CA (US); James L. Figarola, Hacienda Heights, CA (US)

(73) Assignee: City of Hope, Duarte, CA (US)

( * ) Notice: Subject to any disclaimer, the term of this patent is extended or adjusted under 35 U.S.C. 154(b) by 682 days.

(21) Appl. No.: 12/139,822

(22) Filed: Jun. 16, 2008

(65) Prior Publication Data
US 2009/0030081 A1 Jan. 29, 2009

Related U.S. Application Data

(60) Provisional application No. 60/944,362, filed on Jun. 15, 2007.

(51) Int. Cl.
*A61K 31/195* (2006.01)
*A61K 31/19* (2006.01)
(52) U.S. Cl. .................. 514/563; 514/571; 514/866
(58) Field of Classification Search .............. 514/563, 514/571, 866
See application file for complete search history.

(56) References Cited

U.S. PATENT DOCUMENTS

| | | | |
|---|---|---|---|
| 4,921,997 A | 5/1990 | Lalezari et al. | |
| 5,093,367 A | 3/1992 | Lalezari et al. | |
| 5,268,500 A | 12/1993 | Lalezari et al. | |
| 5,272,176 A | 12/1993 | Ulrich et al. | |
| 5,292,935 A | 3/1994 | Lalezari et al. | |
| 5,677,330 A | 10/1997 | Abraham et al. | |
| 5,962,651 A | 10/1999 | Lalezari et al. | |
| 6,337,350 B1 | 1/2002 | Rahbar et al. | |
| 6,589,944 B1 | 7/2003 | Rahbar | |
| 6,605,642 B2 * | 8/2003 | Rahbar et al. | 514/563 |
| 6,787,566 B2 * | 9/2004 | Rahbar | 514/563 |
| 7,320,988 B2 | 1/2008 | Rahbar et al. | |
| 7,652,037 B2 * | 1/2010 | Rahbar et al. | 514/311 |
| 2007/0117819 A1 | 5/2007 | Rahbar et al. | |

FOREIGN PATENT DOCUMENTS

WO 95/31192 A1 11/1995

OTHER PUBLICATIONS

Rahbar et al., "Novel inhibitors of advanced glycation endproducts", Archives of Biochemistry and Biophysics, vol. 419, No. 1, pp. 63-79 (2003).*
Figarola et al., "LR-90 prevents dyslipidaemi and diabetic nephropathy in the Zucker diabetic fatty rat", Diabetologia, vol. 51, No. 5, pp. 882-891 (2008).*
Rahbar, S. et al., "Novel Inhibitors of Advanced Glycation Endproducts," Biochemistry and Biophysics, 419:63-79, 2003.
Tanji, N. et al., "Expression of Advanced Glycation End Products and Their Cellular Receptor RAGE in Diabetic Nephropathy and Nondiabetic Renal Disease," Journal of American Society of Nephrology, 11:1656-1666, 2000.
Tan, A.L. et al., "AGE, RAGE, and ROS in Diabetic Nephropathy," Seminars in Nephrology, 27:130-143, 2007.
Peterson, R.G. et al., "Zucker Diabetic Fatty Rat as a Model for Non-Insulin Dependent Diabetes Mellitus," ILAR Journal, vol. 32, No. 3, 1990, 5 pages.
Kasiske, B.L. et al., "The Zucker Rat Model of Obesity, Insulin Resistance, Hyperlipidemia, and Renal Injury," Hypertension 19 (Suppl 1):I110-I115, 1992.
Chander, P.N. et al., "Nephropathy in Zucker Diabetic Fat Rat is Associated with Oxidative and Nitrosative Stress: Prevention by Chronic Therapy with a Peroxynitrite Scavenger Ebselen," Journal of American Society of Nephrology, 15:2391-2403, 2004.
Mizuno, M. et al., "Renoprotective Effects of Blockade of Angiotensin II AT1 Receptors in an Animal Model of Type 2 Diabetes," Hypertension Research, 25:271-278, 2002.
Rahbar, S., "Novel Inhibitors of Glycation and AGE Formation," Cell Biochemistry and Biophysics, 48:147-157, 2007.
Figarola, J.L. et al., "LR-90 A New Advanced Glycation Endproduct Inhibitor, Prevents Progression of Diabetic Nephropathy in Streptozotocin Diabetic Rats," Diabetologia, 46:1140-1152, 2003.
Rahbar, S. et al., "Inhibitors and breakers of advanced glycation endproducts (AGEs): A review," Curr. Med. Chem. Immunol. Edocr. Metabol. Agents, 2002; 2:135-161.
Vlassara, H. "The AGE-receptor in the pathogenesis of diabetic complications," Diabetes Metab. Res. Rev., 2001, 17:436-443.
Figarola, J.L. et al., "Antiinflammatory Effects of the Advanced Glycation End Product Inhibitor LR-90 in Human Monocytes," Diabetes, 56:647-655, 2007.
Forbes, et al., "Reduction of the Accumulation of Advanced Glycation End Products by ACE Inhibition in Experimental Diabetic Nephropathy," Diabetes, 51:3274-3282, 2002.
Lalezari, I. et al., "LR16, a compound with potent effects on the oxygen affinity of hemoglobin, on blood cholesterol, and on low density lipoprotein," Proc. Natl. Acad. Sci. USA, Aug. 1998; 85:6117-6121.
Rahbar, S. et al., "Novel Inhibitors of Advanced Glycation Endproducts (Part II)," Molecular Cell Biology Research Communications, 2000, vol. 3, pp. 360-366, copyright 2000 by Academic Press.
Friedman, "Advanced Glycation End-products in Diabetic Nephropathy," Nephrology Dialysis Transplantation 14 (Suppl 3):1-9, 1999.
Makita et al., "Advanced Glycosylation End Products in Patients with Diabetic Nephropathy," New England Journal of Medicine, 325:836-842, 1991.
Nangaku et al., "Anti-Hypertensive Agents Inhibit In Vivo the Formation of Advanced Glycation End Products and Improve Renal Damage in a Type 2 Diabetic Nephropathy Rat Model," Journal of American Society of Nephrology, 14:1212-1222, 2003.
Vlassara et al., "Diabetes and Advanced Glycation Endproducts," Journal of Internal Medicine, 251:87-101, 2002.
Nakamura, S. et al., "Progression of Nephropathy in Spontaneous Diabetic Rats is Prevented by OPB-9195, a Novel Inhibitor of Advanced Glycation," Diabetes, 46:895-899, May 1997.

* cited by examiner

*Primary Examiner* — Kevin E Weddington
(74) *Attorney, Agent, or Firm* — Rothwell, Figg, Ernst & Manbeck P.C.

(57) ABSTRACT

The present invention provides methods for ameliorating, overcoming, or inhibiting insulin resistance in a subject, comprising administering to the subject an effective amount of a compound selected from the group consisting of LR-90 and LR-102, or a pharmaceutically acceptable salt or derivative thereof. Methods of treating type 2 diabetes and diabetic nephropathy, or preventing or slowing their development are also encompassed by the invention.

7 Claims, 14 Drawing Sheets
(11 of 14 Drawing Sheet(s) Filed in Color)

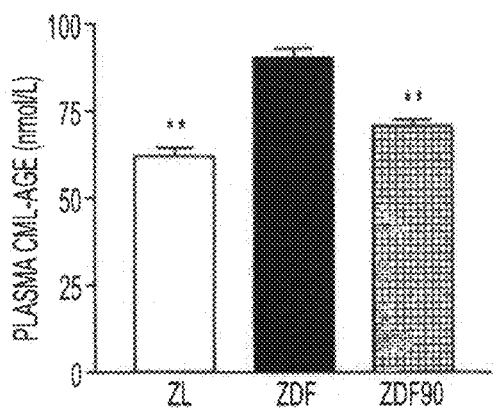 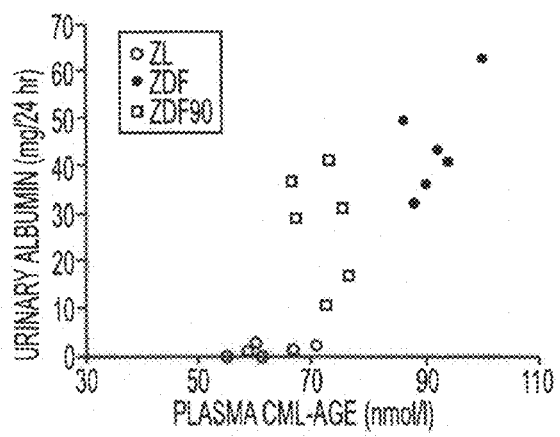
FIG. 5a　　　　　　　FIG. 5b
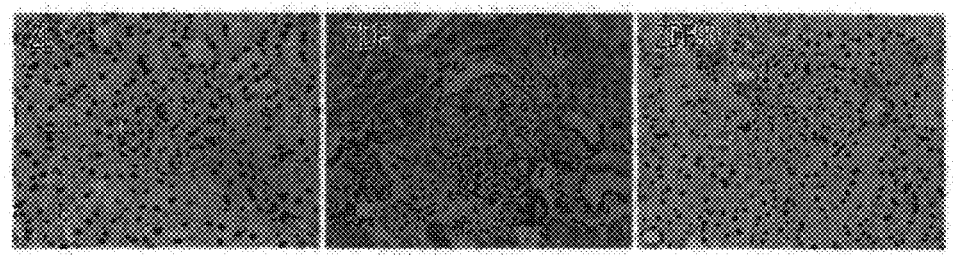
FIG. 5c
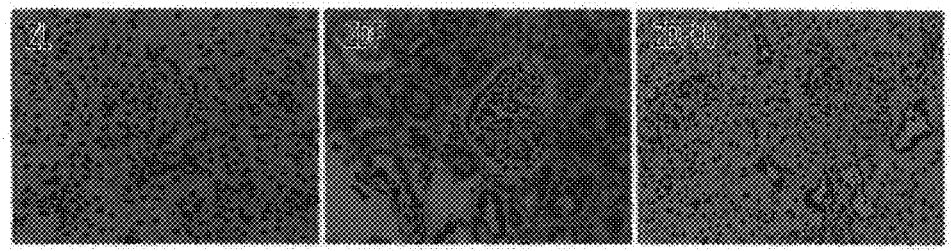
FIG. 5d
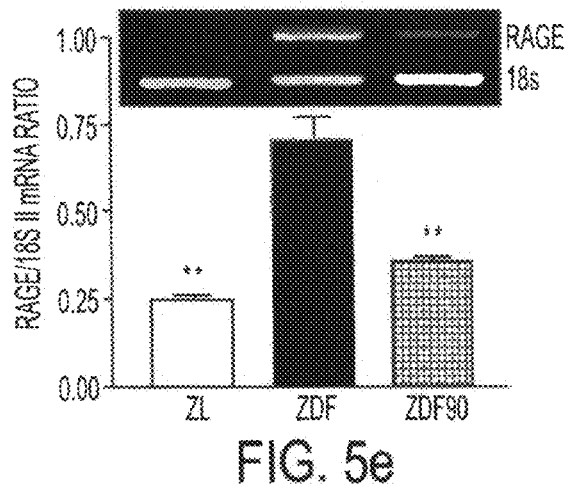
FIG. 5e

USE OF LR-90 AND LR-102 TO OVERCOME INSULIN RESISTANCE

CROSS-REFERENCE TO RELATED APPLICATION

The present application claims benefit under 35 U.S.C. §119 of U.S. Provisional Patent Application No. 60/944,362, filed Jun. 15, 2007, which application is incorporated herein by reference in its entirety.

FIELD OF THE INVENTION

The present invention relates generally to the field of biomedical sciences, and in particular to certain compounds previously identified as AGE inhibitors, and methods for their use.

BACKGROUND OF THE INVENTION

All United States patents and patent applications referred to herein are hereby incorporated by reference in their entireties into the present application. In particular, U.S. Pat. Nos. 6,337,350, 6,589,944, 6,605,642, and 6,787,566, 7,320,988, and U.S. Patent Application Publication 2007/0117819A1 (U.S. application Ser. No. 11/594,981), which refer to various compounds, including LR-90 and LR-102, processes for their preparation, and their uses, are hereby incorporated by reference in their entireties. Moreover, throughout this application, various publications are referenced, which, along with the above-referenced patents and applications, illuminate the background of the invention or provide additional details respecting the practice. These publications also are hereby incorporated by reference in their entireties into the present application. Full bibliographic citations for the publications can be found listed immediately preceding the claims. In the case of conflict between any of the incorporated references and the present specification, the present specification, including definitions, will control.

Glucose and other reducing sugars react and bind covalently to proteins, lipoproteins and DNA by a process known as non-enzymatic glycation. Glucose latches onto tissue proteins by coupling its carbonyl group to a side-chain amino group such as that found on lysine. Over time, these adducts form structures called advanced glycation endproducts (AGEs) (protein-aging). These cross-linked proteins stiffen connective tissue and can lead to tissue damage in the kidney, retina, vascular wall and nerves.

In human diabetic patients and in animal models of diabetes, these non-enzymatic reactions are accelerated and cause accumulation of AGEs on long-lived structural proteins, such as collagen, fibronectin, tubulin, lens crytallin, myelin, laminin and actin, in addition to hemoglobin, albumin, LDL-associated proteins and apoprotein. The structural and functional integrity of the affected molecules, which often play major roles in cellular functions, are perturbed by such modifications, with severe consequences on organs such as kidney, eye, nerve, and micro-vascular functions (as noted above). This consequently leads to various diabetic complications, including nephropathy, atherosclerosis, microangiopathy, neuropathy and retinopathy. Boel et al., *J. Diabetes Complications* 9:104-129, 1995; Hendrick et al., *Diabetologia* 43:312-320, 2000; Vlassara and Palace, *J. Intern. Med.* 251: 87-101, 2002. AGEs thus have been implicated in the pathogenesis of a variety of debilitating diseases such as diabetes, atherosclerosis, Alzheimer's and rheumatoid arthritis, as well as in the normal aging process. Most recent researchers confirm a significant role of the accumulation of AGE cross-links in promoting the decreased cardiovascular compliance of aging (Asif et al., 2000).

In recent years, several promising therapeutic drugs that could inhibit or break the AGE crosslinks in tissues and cells, and thus prevent their consequences, have been reported. Both inhibitors of AGE formation and AGE-breakers not only may have a beneficial effect in reducing complications of AGE-related diseases, AGE-breakers may cure the disease by removing AGEs from damaged tissues and cells. U.S. Pat. No. 6,787,566, (and other patents incorporated by reference herein) describes several compounds that have been found to be active in breaking AGE-protein cross-links, including methylene bis[4,4'-(2-chlorophenylureidophenoxyisobutyric acid)] ("LR-90") and 1,4-benzene-bis[4-methyleneaminophenoxyisobutyric acid] ("LR-102").

Diabetic nephropathy is one of the most serious complications of diabetes and its incidence is increasing dramatically worldwide. It is now the leading cause of end-stage renal failure and the requirement for chronic dialysis or renal replacement therapy [1, 2]. The characteristic features of diabetic nephropathy include persistent albuminuria, a progressive decline in renal function and, histopathologically, mesangial expansion followed by glomerulosclerosis and interstitial fibrosis [3, 4]. Although the pathological and clinical indices of diabetic nephropathy are well described, the precise molecular mechanisms underlying its pathogenesis are not completely understood. Over the last decade, evidence has accumulated, implicating AGE and AGE-protein crosslinking as a major factor in the progression of diabetic nephropathy [5, 6]. Several studies have shown that the extent of AGE formation, particularly AGE adducts in glomerular and tubulointerstitial compartments, correlates with the severity of diabetic nephropathy [7, 8]. AGE may contribute to diabetic tissue injury by a number of different pathways, including receptor-independent alterations of the extracellular matrix (ECM) architecture and protein cross-linking, as well as by modulating expression of various inflammatory genes, cytokines and growth factors through cell surface receptors, including the receptor for AGE (AGER) [9, 10]. Previous studies have shown that LR-90 prevented the development of experimental type 1 diabetic nephropathy. (24).

Prospective studies of the natural history of type 2 diabetes have shown that the prediabetic state is characterized by resistance to insulin-mediated glucose disposal and compensatory hyperinsulinemia. The transition from pre-diabetes to Type 2 diabetes occurs when the secretory capacity of the pancreatic d cell is no longer able to compensate for the insulin resistance. Resistance to insulin action is a common abnormality present in major human diseases such as diabetes mellitus and obesity. Abdominal obesity contributes to insulin resistance, a metabolic abnormality linked to the development of type 2 diabetes and cardiovascular disease. Insulin resistance generally precedes the development of type 2 diabetes. Currently, an estimated 20.5 million US adults have diabetes and another 54 million have impaired glucose tolerance, an intermediate step between insulin resistance and diabetes.

Accordingly, there currently exists a need in the art for methods of ameliorating or inhibiting insulin resistance in a subject, particularly a subject who has type 2 diabetes or is in a prediabetic state. There is also a need for prevention of the development of type 2 diabetes and type 2 diabetic nephropathy, including those instances in which multiple risk factors, such as hyperglycemia, dyslipidemia, obesity, insulin resistance, or hypertension, contribute to renal injury.

SUMMARY OF THE INVENTION

The present invention relates to compounds and methods useful in treating conditions that occur during or prior to development of type 2 diabetes.

In an aspect, the present invention provides methods of ameliorating, inhibiting and/or overcoming insulin resistance in a subject, comprising administering to the subject an effective amount of a compound (or a pharmaceutically acceptable salt or derivative thereof) which is preferably LR-90 (methylene bis[4,4'-(2-chlorophenylureidophenoxyisobutyric acid)]) or LR102 (1,4-benzene-bis[4-methyleneaminophenoxyisobutyric acid]). The subject can be any organism but is preferably a mammal, more preferably a human. In embodiments, the subject has type 2 diabetes or is in a prediabetic state. Thus, the invention also provides methods of treating or preventing type 2 diabetes, and methods of treating or preventing diabetic nephropathy in a subject in need of such treatment or prevention. In particular, LR-90, an AGE inhibitor with pleiotrophic effects, may be used in accordance with the invention for prevention of type 2 diabetic nephropathy, where multiple risk factors, such as hyperglycaemia, dyslipidaemia, obesity, insulin resistance and hypertension, contribute to renal injury.

Accordingly, the present invention encompasses methods of administering compounds such as LR-90 and LR-102, their pharmaceutical salts, or derivatives, to a subject for the treatment or prevention of conditions including type 2 diabetes and type 2 diabetic nephropathy, wherein the administration inhibits, ameliorates, or overcomes insulin resistance or other risk factors associated with such conditions.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 5. LR-90 inhibits AGE formation and AGER activation. Circulating plasma CML-AGE (a) was measured using ion-pair reversed-phase liquid chromatography/tandem mass spectrometry. Correlation analysis (b) showed strong association between CML-AGE and urinary albumin excretion ($r=0.82$, $p<0.0001$, if data were merged from all three groups). White circles, ZL; black circles, ZDF; white squares, ZDF90. Immunohistochemical stainings demonstrated that renal AGE (c) and (d) AGER protein formation in ZDF rats were also reduced by LR-90 treatment. Original magnification ×320. Expression of renal Ager, as determined by RT-PCR (e), was also suppressed by LR-90. **$p<0.01$ vs ZDF (n=4). ZDF90, LR-90-treated ZDF rats.

DETAILED DESCRIPTION OF THE INVENTION

Figure 1A:
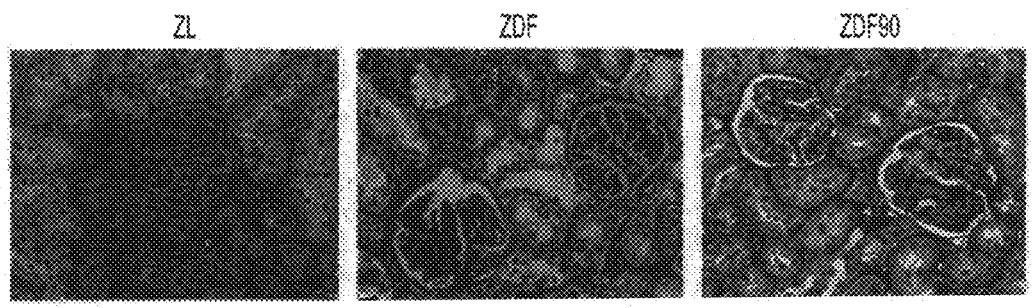
FIG. 1. LR-90 ameliorates renal injury in ZDF rats. Representative photomicrographs of (a) PAMS staining (original magnification, ×320) showing increased positive staining inside glomeruli in ZDF rats and its reduction by LR-90, and (b) Masson's trichrome staining (original magnification, ×100) demonstrating tubular degeneration and interstitial and glomerular collagen deposition in ZDF rats and its attenuation by LR-90. Quantitative scoring for (c) PAMS staining, (d) glomerulosclerosis index (GSI), (e) tubular degeneration and (f) percentage positive collagen area staining were all reduced significantly by LR-90 treatment. **$p<0.01$ vs ZDF rats (n=4-6). ZDF90, LR-90-treated ZDF rats.

Several compounds have been previously described as being active in binding AGE-protein crosslinks. Two such compounds, LR-90 and LR-102 (and pharmaceutical salts and derivatives thereof), have been described, for example, in U.S. Pat. No. 6,787,566, (and other patents and publications) incorporated herein by reference.

The present invention provides methods of ameliorating, inhibiting and/or overcoming insulin resistance in a subject, comprising administering to the subject an effective amount of a compound, which is preferably LR-90 (methylene bis[4,4'-(2-chlorophenylureidophenoxyisobutyric acid)]) or LR102 (1,4-benzene-bis[4-methyleneaminophenoxyisobutyric acid]). The subject can be any organism, but is preferably a mammal, more preferably a human. In embodiments, the subject has type 2 diabetes or is in a prediabetic state. Thus, the invention also provides methods of treating or preventing type 2 diabetes, and methods of treating or preventing diabetic nephropathy in a subject in need of such treatment or prevention. In particular, LR-90, an AGE inhibitor with pleiotrophic effects, may be used in accordance with the invention for prevention of type 2 diabetic nephropathy, where multiple risk factors, such as hyperglycaemia, dyslipidaemia, obesity, insulin resistance and hypertension, contribute to renal injury.

Accordingly, the present invention encompasses methods of administering compounds such as LR-90 and LR-102, their pharmaceutical salts, or derivatives, to a subject for the treatment or prevention of conditions including type 2 diabetes and type 2 diabetic nephropathy, wherein the administration inhibits, ameliorates, or overcomes insulin resistance or other risk factors associated with such conditions. A method for treating or preventing Type 2 diabetic nephropathy in a subject, comprising administering to the subject an effective amount of a compound selected from the group consisting of LR-90 and LR-102 or a pharmaceutically acceptable salt or derivative thereof. The compound is preferably LR-90.

The invention also encompasses the administration of pharmaceutically acceptable salts and derivatives of the compounds, as well as compositions comprising the compounds (or these salts or derivatives) and pharmaceutically acceptable carriers or excipients. Accordingly, the present invention encompasses methods of treating diabetes in a patient by administering to a patient in need thereof, an effective amount of a compound, such as LR-90 or LR-102, a pharmaceutically acceptable salt or derivative thereof, or a composition comprising such compounds, salts or derivatives.

In an aspect of the invention, administration of the compounds, salts or derivatives thereof, or compositions described herein, provides benefits in FFA uptake, glucose uptake, glucose metabolism, insulin sensitivity, or reduction of Islet cell damage in the subject.

The studies provided herein show that LR-90 in particular can be useful in the treatment, amelioration, or prevention of insulin resistance, Type 2 diabetes or diabetic nephropathy, or the prevention or slowing of the development of these conditions, as it can, inter alia, reduce hyperlipidemia, attenuate an increase in C-reactive protein (CRP), reduce plasma insulin, provide benefits with respect to insulin sensitivity, prevent or diminish damage to insulin-secreting islet cells in the pancreas, prevent accumulation of lipid peroxidation products in the kidney, retard the increase in albuminuria and proteinuria, improve FFA and glucose uptake, and prevent renal oxidative stress. LR-90, in particular, can therefore be useful in attenuating renal injury by modulating several metabolic factors involved in the pathogenesis of diabetic nephropathy.

Accordingly, the compounds referred to herein, their pharmaceutically acceptable salts and derivatives, and compositions comprising such compounds, salts, and derivatives can be useful in providing benefits to those suffering from or at risk of developing Type 2 diabetes and associated complications.

Dosages and effective amounts for administration of the compounds and compositions in the methods described herein can be readily determined by those of skill in the art by reference to the present disclosure (including that incorporated by reference) and in concert with the ordinarily skilled artisan's general knowledge and skill in the art.

In that regard, pharmaceutical compositions containing a compound of the present invention or its pharmaceutically acceptable salts as the active ingredient can be prepared according to conventional pharmaceutical compounding techniques. See, for example, *Remington's Pharmaceutical Sciences,* 18th Ed. (1990, Mack Publishing Co., Easton, Pa.). Typically, an effective amount of the active ingredient will be admixed with a pharmaceutically acceptable carrier. The carrier may take a wide variety of forms depending on the form of preparation desired for administration, e.g., intravenous, oral or parenteral.

The term "salt", as used herein, denotes acidic and/or basic salts, formed with inorganic or organic acids and/or bases, preferably basic salts. While pharmaceutically acceptable salts are preferred, particularly when employing the compounds of the invention as medicaments, other salts find utility, for example, in processing these compounds, or where non-medicament-type uses are contemplated. Salts of these compounds may be prepared by art-recognized techniques.

Examples of such pharmaceutically acceptable salts include, but are not limited to, inorganic and organic addition salts, such as hydrochloride, sulphates, nitrates or phosphates and acetates, trifluoroacetates, propionates, succinates, benzoates, citrates, tartrates, fumarates, maleates, methane-sulfonates, isothionates, theophylline acetates, salicylates, respectively, or the like. Lower alkyl quaternary ammonium salts and the like are suitable, as well.

As used herein, the term "pharmaceutically acceptable" carrier means a non-toxic, inert solid, semi-solid, liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, alpha-tocopherol and the like; and the metal chelating agents such as citric acid, ethylenediamine tetraacetic acid (EDTA), sorbitol, tartaric acid, phosphoric acid and the like.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable for passage through the gastrointestinal tract, while at the same time allowing for passage across the blood brain barrier.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, stabilizing agents, buffers and the like. One particularly suitable stabilizing agent for the conotoxin peptides contemplated here is carboxymethyl cellulose. This agent may be particularly effective due to the excess positive charge of the contemplated conotoxin peptides. When the compounds are being administered intrathecally, they may also be dissolved in cerebrospinal fluid.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, epidural, irrigation, intramuscular, release pumps, or infusion.

The active agent is preferably administered in a pharmacologically or therapeutically effective amount. By a "pharmacologically effective amount" or "therapeutically effective amount" or simply "effective amount" of an active compound is meant a sufficient amount of the compound to achieve the desired effects described herein. The actual amount administered, and the rate and time-course of administration, will depend on the nature and severity of the condition being treated. The administration may be continuous or be intermittent. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences*.

Data can be obtained, including as described herein, from cell culture assays and animal studies, to formulate a suitable dosage range for humans. Dosage may be adjusted appropriately to achieve desired drug levels, locally or systemically. A suitable dose can be administered in multiple sub-doses per day. Dosages are generally initiated at lower levels and increased until desired effects are achieved.

Advantageously, the compositions are formulated as dosage units, each unit being adapted to supply a fixed dose of active ingredients. Tablets, coated tablets, capsules, ampoules and suppositories are examples of dosage forms according to the invention.

It is only necessary that the active ingredient constitute an effective amount, i.e., such that a suitable effective dosage will be consistent with the dosage form employed in single or multiple unit doses. The exact individual dosages, as well as daily dosages, are determined according to standard medical principles under the direction of a physician or veterinarian for use humans or animals.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982*, Molecular Cloning* (Cold Spring Harbor Laboratory Press, Cold Spring Harbor, N.Y.); Sambrook et al, 1989*, Molecular Cloning,* 2nd Ed. (Cold Spring Harbor Laboratory Press, Cold Spring Harbor, N.Y.); Sambrook and Russell, 2001*, Molecular Cloning,* 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985*, DNA Cloning* (IRL Press, Oxford); Russell, 1984*, Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988*, Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference* (RNAi): *The Nuts & Bolts of siRNA Technology*, DNA Press, 2003; Gott, *RNA Interference, Editing, and Modification: Methods and Protocols* (*Methods in Molecular Biology*), Human Press, Totowa, N.J., 2004; Sohail, *Gene Silencing by RNA Interference: Technology and Application*, CRC, 2004.

In light of the preceding description, one of ordinary skill in the art can practice the invention to its fullest extent. The following examples, therefore, are merely illustrative and should not be construed to limit in any way the invention as set forth in the claims which follow.

EXAMPLES

The following abbreviations are used throughout the present disclosure, including the Examples provided herein:
AGER receptor for AGE
ARB angiotensin TI receptor blocker
CML Nε-(carboxymethyl)lysine
CTGF connective tissue growth factor
ECM extracellular matrix
MAPK mitogen-activated protein kinase
NF-κB nuclear factor-kappa B
PAMS periodic acid-Schiff-methenamine silver
ZDF Zucker diabetic fatty
ZL Zucker lean The Zucker diabetic fatty (ZDF) rat is considered to be an excellent animal model of obesity and type 2 diabetes, presenting a physiological and metabolic profile similar to that seen in humans. The ZDF rat is characterised by hyperglycaemia, hyperinsulinaemia, hyperlipidaemia, both moderate hypertension and obesity, and progressive renal injury [11, 12]. These rats develop albuminuria at about 14 weeks, begin exhibiting glomerulosclerosis by 18 to 20 weeks and have increasing proteinuria resulting in chronic renal insufficiency by 22 weeks of age relative to their genetic lean controls [13-15]. The nephropathy in this model has been described as focal segmental glomerulosclerosis associated with glomerulomegaly and mesangial expansion [14, 15]. Previous studies have shown that the development of diabetic nephropathy in obese ZDF rats can be ameliorated by treatment with peroxisome proliferator-activated receptor-gamma agonists [16, 17], ACE inhibitors and angiotensin TI receptor blockers (ARBs) [18, 19], vasopeptidase inhibitors [19, 20], antivascular endothelial growth factor antibodies [21] and antioxidants [15]. These intervention studies suggest that the pathogenesis of renal damage in type 2 diabetes involves a complex interrelationship of metabolic and/or haemodynamic factors.

Example 1

LR-90 Prevents Dyslipidaemia and Diabetic Nephropathy in the Zucker Diabetic Fatty Rat As noted, previous studies have shown that LR-90, a new inhibitor of AGE formation, prevented the development of experimental type 1 diabetic nephropathy. In the present Example, the effects of LR-90 were examined in the Zucker diabetic fatty (ZDF) rat, a model of type 2 diabetes and metabolic syndrome, and the mechanisms by which it may protect against renal injury were investigated. In this Example, male ZDF rats were treated without or with LR-90 from age 13 to 40 weeks. Metabolic and kidney functions and renal histology were evaluated. AGE accumulation and the production of the receptor for AGE (AGER) were measured. Profibrotic growth factors, extracellular matrix proteins and intracellular signalling pathways associated with glomerular and tubular damage were also analysed. Results show that LR-90 dramatically reduced plasma lipids in ZDF rats, with only modest effects on hyperglycaemia. RenalAGE, AGER and lipid peroxidation were all attenuated by LR-90. LR-90 significantly retarded the increase in albuminuria and proteinuria. This was associated with reduction in glomerulosclerosis and tubulointerstitial fibrosis, concomitant with marked inhibition of renal overproduction of TGF-β1, connective tissue growth factor, fibronectin and collagen IV. Additionally, LR-90 downregulated the activation of key mitogen-activated protein kinases (MAPKs) and nuclear factor kappa B (NF-κB) in the renal cortex.

Previously, we reported new classes of compounds as inhibitors of AGE formation and protein cross-linking [22, 23]. More recently, several of these compounds were found effective in preventing the development of diabetic nephropathy in streptozotocin-induced diabetic animals [24, 25]. In the present study, we evaluated whether LR-90, one of the more powerful AGE inhibitors with other biochemical effects (lipid-lowering, antioxidant, anti-inflammatory) [22, 23, 26], can prevent dyslipidaemia and the development of renal dysfunction in experimental models of type 2 diabetes. We also investigated the effects of LR-90 on the production of pro-sclerotic and profibrotic growth factors and ECM proteins and their intracellular signalling pathways in the kidney to explore the possible mechanisms responsible for the renoprotective effects of LR-90 on diabetic nephropathy in ZDF rats.

Methods/Materials

Unless otherwise noted, all chemicals and reagents were obtained from Sigma (St. Louis, Mo., USA). The Nephrat albumin kit was from Exocell (Philadelphia, Pa., USA). Monoclonal antibodies against AGE and TGF-β1 were purchased from CosmoBio (Tokyo, Japan) and R&D Systems (Minneapolis, Minn., USA), respectively. Polyclonal anti-AGER and connective tissue growth factor (CTGF) antibodies were from Novus Biologicals (Littleton, Colo., USA), while antiphospho-p38 mitogen-activated protein kinase (MAPK), p38 MAPK, p44/42 MAPK (ERK 1/2), and anti nuclear factor-kappa B (NF-κB) antibodies were purchased from Cell Signaling Technology (Beverly, Mass., USA). Anti-fibronectin, anti-collagen IV and anti-histone H2B polyclonal antibodies were obtained from Abcam (Cambridge, Mass., USA), Cedarlane Laboratories (Burlington, ON, Canada) and Upstate Biotechnology (Lake Placid, N.Y., USA), respectively. All other immunohistochemical reagents were obtained from DakoCytomation (Carpinteria, Calif., USA) and Vector Laboratories (Burlingame, Calif., USA).

Experimental Animals

All animal studies were carried out in compliance with policies outlined in The Guide for the Care and Handling of Laboratory Animals (NIH Publication No. 85-23) that have been approved by the City of Hope Animal Care Committee. Male ZDF (fa/fa) and male Zucker lean (+/+; ZL) rats were obtained at the age of 5 weeks from Charles River Laboratories (Wilmington, Mass., USA). Animals were maintained with free access to Purina 5008 rat chow (Purina Mills, St Louis, Mo., USA) and tap water. All animals were individually housed in a controlled room with a 12 h dark-light cycle. At the age of 13 weeks, the animals were divided into the following groups: (1) ZL rats (n=6); (2) ZDF rats without treatment (n=6); and (3) ZDF rats treated with LR-90 at 50 mg/l in their drinking water (ZDF90, n=6). The dose of LR-90 was chosen after previous experiments with type 1 diabetic nephropathy [25]. Food, water intake, body weight and blood glucose levels were monitored periodically. Systolic blood pressure was measured by tail-cuff plethysmography (CODA2 Blood Pressure System; Kent Scientific, Torrington, Conn., USA). Animals were killed at the age of 40 weeks by over-anaesthetisation with isoflurane and cardiac puncture. Blood samples were collected from each animal and transferred accordingly into heparinised vacutainer tubes; they were later centrifuged (1,500×g for 10 min at 4° C.) for plasma isolation. The kidneys were removed immediately, rinsed in PBS and weighed, after which specimens were snap-frozen in liquid nitrogen or fixed in 10% (vol./vol.) neutral buffered formalin for further biochemical and histological analyses. Plasma glucose, lipids and Nε-(carboxymethyl)lysine-AGE Plasma glucose was measured using a glucose analyzer (2300 STAT; YSI, Yellowsprings, Ohio, USA). Total plasma triacylglycerol and cholesterol concentrations were quantified using the Vitros 250 Chemistry System (Johnson & Johnson, Rochester, N.Y., USA). Nε-(Carboxymethyl)lysine (CML)-AGE was liberated from plasma proteins by acid hydrolysis and then measured by ion-pair reversed-phase liquid chromatography/tandem mass spectrometry as described previously [24].

Renal Function

Renal function was assessed by measuring urinary albumin and total protein excretion. Prior to killing, rats were housed in metabolism cages for 24 h urine collection. Urinary albumin was quantified using the Nephrat kit according to manufacturer's instructions. Total urinary protein was measured using a kit (DC Assay; Bio-Rad Laboratories, Hercules, Calif., USA).

Kidney Histopathology

Kidney sections were stained with periodic acid-Schiff-methenamine silver (PAMS) to evaluate glomerulosclerosis and mesangial matrix expansion; Masson's trichrome staining was used to analyse collagen deposition and cortical tubule degeneration. Glomerulosclerosis was defined as glomerular basement membrane thickening, mesangial hypertrophy and capillary occlusion, and was semiquantitatively evaluated on an arbitrary scale of 0 to 4: grade 0 (normal); grade 1 (sclerotic area less than 25%); grade 2 (sclerotic area 25-50%); grade 3 (sclerotic area 50-75%); and grade 4 (sclerotic area more than 75%). The glomerulosclerotic index was then calculated as described [27]. Briefly, 100 glomeruli were randomly chosen from each rat kidney stained with PAMS and carefully scored for sclerosis by two blinded investigators. This was done in a sequential manner to ensure that the same glomerulus was not graded twice. To quantify for mesangial expansion and ECM accumulation in the mesangial areas, PAMS-positive materials in the mesangial region excluding cellular elements were analysed using an image analyser with a microscope (Olympus AX70; Olympus Optical, Hamburg, Germany) and photographed using a Retiga 2000R CCD camera (Qimaging, Surrey, BC, Canada). Twenty glomeruli, randomly selected from each rat were evaluated by two investigators without knowledge of the origin of the slides. The percentage of PAMS-positive area in each glomerulus was analysed using Image Pro Plus (Media Cybernetics, Silver Spring, Mass., USA). Results were expressed as percentage of areas positive for PAMS staining.

To evaluate cortical tubule degeneration and collagen deposition, kidney sections were stained with Masson's trichrome. In each section, six fields of kidney cortex were randomly selected at 100× magnification using an Olympus AX70 microscope, photographed using a Retiga 2000R camera and the images analysed by Image Pro Plus. Blue and red colours indicate collagen and cytoplasm staining, respectively. Degenerate tubules in each field were identified by the absence of cytoplasm and results expressed as number of degenerate tubules per field [27]. For quantitative measurement of collagen deposition, positively stained areas from six random regions in each slide were identified and scored by dividing the positively stained areas by the total tissue area in the same field using the colour separation function of Image Pro Plus. Results were expressed as percentage of area with positive staining.

Immunohistochemistry

Tissue sections were deparaffinised by sequential exposure to xylene and ethanol, dehydrated and then exposed to $H_2O_2$ to eliminate endogenous peroxidase activity. The kidney sections were then blocked with 2% (wt/vol.) BSA and exposed to specific antibodies against AGE, AGER, TGF-β1, CTGF, fibronectin and collagen type IV. Biotinylated anti-rabbit or anti-mouse IgG was then applied as a secondary antibody, followed by horseradish peroxidase conjugated streptavidin. The staining was visualised by reaction with 3,3'-diaminobenzidine tetrahydrochloride and then counterstained with haematoxylin. All the sections were examined by light microscopy (Olympus AX70) and photographed with Retiga 2000R camera.

Tissue Extraction

Renal cortical tissues were homogenised in PBS buffer with 1% (vol./vol.) Nonidet P-40, 0.5% (wt/vol.) sodium deoxycholate, 0.1% (wt/vol.) SDS and protease inhibitor mixture (Roche, Indianapolis, Ind., USA). Homogenates were centrifuged for 15 min at 4° C. and at 12,000 rpm and the supernatant fractions collected and stored at −70° C. Nuclear extracts were prepared as described previously [28]. Protein concentrations were measured using the Bio-Rad DC Assay kit. Total RNA was isolated using the RNA-STAT-60 reagent (Tel-Test, Friendswood, Tex., USA). Western blot assay Protein samples (50 μg) were separated on 10 to 20% gradient Tris-glycine Criterion gels (Bio-Rad) and then transferred to nitrocellulose membranes. The membranes were blocked with 5% (wt/vol.) skimmed milk in PBS before incubation with anti-TGF-β1, anti-CTGF, anti-AGER, anti-phospho-p38 MAPK, anti-phospho-p44/42 MAPK and anti-p65 NF-κB antibodies. Immunoreactive proteins were detected by enhanced chemiluminescence (Western Lightning Chemiluminescence Reagent; Perkin-Elmer, Waltham, Mass., USA) using horseradish peroxidase-labelled secondary antibodies. Equal amounts of protein loading were confirmed by restaining the membranes with antibodies against β-actin, p38 MAPK or p44/42 MAPK for cytosolic extracts or with histone H2B for nuclear extracts. Band intensities were quantified using a densitometer (Quantity One, Bio-Rad). Reverse transcriptase-polymerase chain reaction Total RNA (1 μg) was used for the RT reaction using the GeneAmp RNA PCR kit (Applied Biosystems, Foster City, Calif., USA). Total cDNA was then used in PCR reactions containing gene specific primers [Electronic supplementary material (ESM) Table 1] paired with Quantum 18S rRNA internal standards (Ambion, Austin, Tex., USA). Multiplex PCR reactions were performed in a GeneAmp 9700 (Applied Biosystems). PCR products were fractionated on 2% (wt/vol.) agarose gel electrophoresis and photographed using AlphaImager 2000 (Alpha Innotech, San Leandro, Calif., USA). The densities of amplified products corresponding to specific genes and 18S rRNA were quantified with Quantity One software (Bio-Rad). Results are expressed as the means of the ratios of Tgfb1, Ctgf or Ager band densities to the 18S rRNA band density.

Kidney Lipid Peroxidation

To assess lipid peroxidation in renal cortical homogenates, malondialdehyde, an end-product of lipid peroxidation, was measured as thiobarbituric acid reactive substances by calorimetric reaction as described [29]. Reaction was carried in the presence of EDTA and antioxidant butylated hydroxytoluene, and the absorbance was measured at 532 nm (UV-1601; Shimadzu Scientific Instruments, Columbia, Md., USA). Hydrolysed 1,1,3,3-tetramethoxypropane was used as standard [prepared by incubating 10 mmol/l tetramethoxypropane with 1% (vol./vol.) $H_2SO_4$ for 2 h at room temperature]. Results are expressed as nanomole malondialdehyde per milligram protein.

Data Analyses

Statistical analyses were performed using Prism (Graph-Pad, San Diego, Calif., USA). Data were first analysed by ANOVA and post hoc comparisons between group means analysed using two-tailed unpaired t test. The strength of the relationship between two variables was assessed by the Pearson correlation test. A p value of less than 0.05 was considered statistically significant. Data are presented as means±SEM.

Results

Metabolic Parameters

Table 1 shows the metabolic data of ZL, ZDF and LR-90 treated ZDF (ZDF90) rats at age 40 weeks. As expected, ZDF rats were hyperglycaemic, hyperlipidaemic, polydipsic and had slightly elevated blood pressure in comparison with their lean ZL counterparts. Body weights and heart rates of the three treatment groups at the time of death were not significantly different from each other. Administration of LR-90 to ZDF rats significantly reduced plasma triacylglycerol and cholesterol by ~55% and ~30%, respectively (p<0.05). LR-90 had only modest, but not statistically significant effects on hyperglycaemia and blood pressure. In addition, body weight was lower in LR-90 treated ZDF rats than in ZDF controls, although the difference was not statistically significant (p=0.061).

Renal Function and Histology

Figure 1B:
Figure 1C:
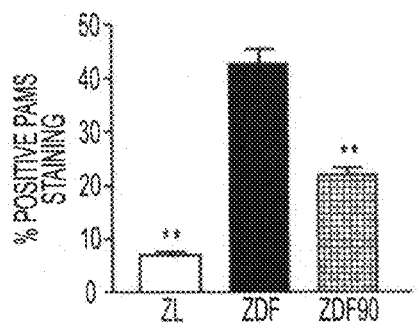
Figure 1D:
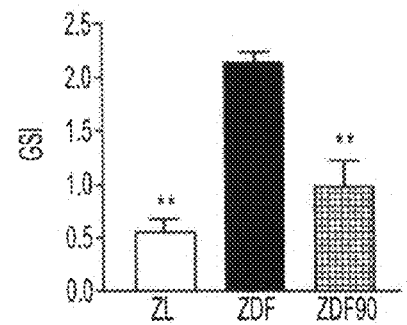
Figure 1E:
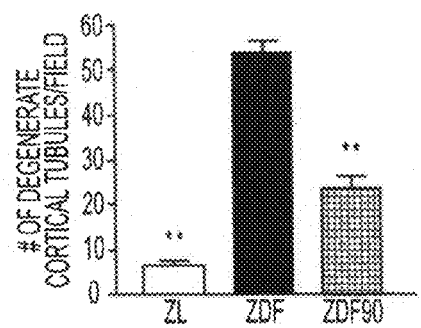
Figure 1F:
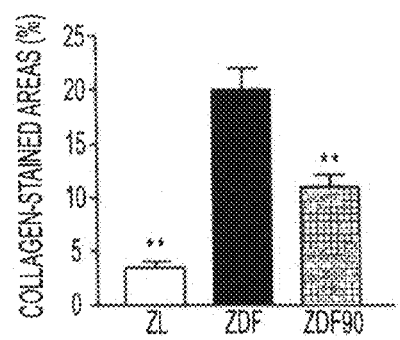
Figure 2A:
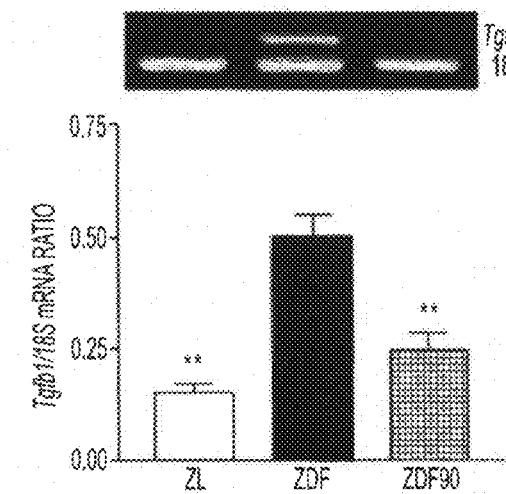
FIG. 2. Tgfb 1 and Ctgf mRNA expression and protein production were reduced by LR-90 treatment. Representative gel profiles (a, b) for RTPCR with quantitative densitometric analyses showing the effects of LR-90 on mRNA expression. c Representative western blot showing protein production in the renal cortex, with (d, e) quantitative densitometric analyses. Values in bar graphs: mean±SEM (n=3-4). **$p<0.01$ vs ZDF. ZDF90, LR-90-treated ZDF rats.
Figure 2B:
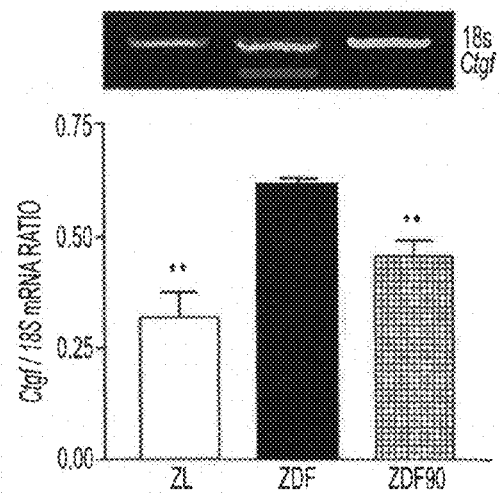
Figure 2C:
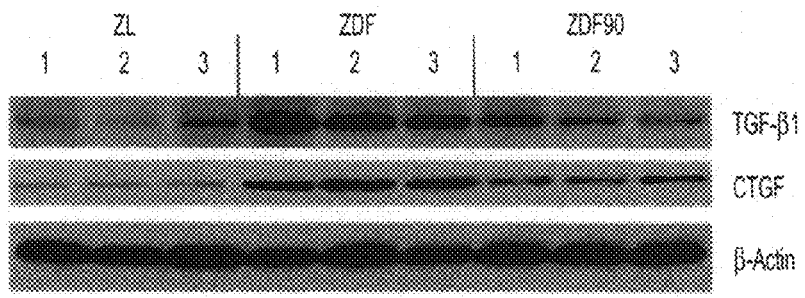
Figure 2D:
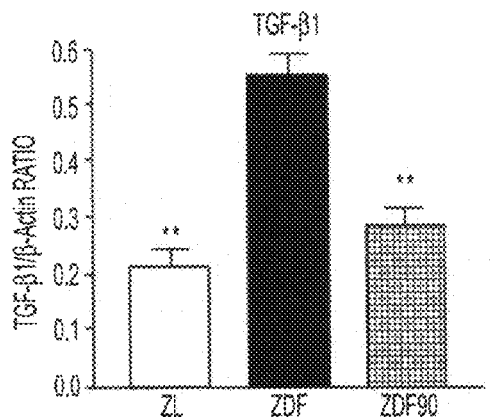
Figure 2E:
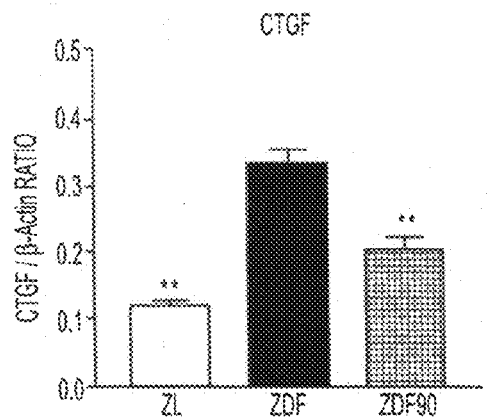

ZDF rats had increased urinary volume output, total urinary protein and albumin excretion compared with lean controls (Table 2). Also, ZDF rats had higher kidney weights (both mean and relative weights) than ZL rats (p<0.001), indicating nephromegaly. In addition, kidneys of ZDF rats exhibited increased mesangial ECM accumulation, glomerulosclerosis and tubulointerstitial injury as evidenced by excessive accumulation of PAMS-positive materials in the mesangial area of the glomeruli (FIG. 1a,c), resulting in higher glomerulosclerotic index scores (FIG. 1d), increased interstitial and glomerular collagen deposition, and tubular degeneration in the renal cortex (FIG. 1b,e,f).

TABLE 1

Metabolic data on Zucker lean (ZL), diabetic fatty (ZDF) and LR-90 treated ZDF (ZDF90) rats at 40 weeks of age.

|  | ZL (n = 6) | ZDF (n = 6) | ZDF90 (n = 6) |
| --- | --- | --- | --- |
| Body Weight (g) | 448 ± 5 | 425 ± 18 | 347 ± 32 |
| Plasma Glucose (mmol/l) | 9.6 ± 0.5** | 29.6 ± 1.3 | 25.0 ± 2.3 |
| Plasma Triglycerides (mmol/l) | 1.9 ± 0.2** | 9.8 ± 2.1 | 4.4 ± 0.6* |
| Plasma Cholesterol (mmol/l) | 2.5 ± 0.2*$^8$ | 8.9 ± 0.9 | 6.3 ± 0.3* |
| Mean Systolic BP (mm Hg) | 140 ± 5* | 158 ± 5 | 144 ± 6 |
| Heart Rate (beats/min) | 340 ± 11 | 341 ± 13 | 330 ± 12 |

*$P < 0.05$ vs. ZDF rats;
**$P < 0.01$ vs. ZDF rats

TABLE 2

Renal function data of Zucker lean (ZL), diabetic fatty (ZDF) and LR-90 treated ZDF (ZDF90) rats at 40 weeks of age.

|  | ZL (n = 6) | ZDF (n = 6) | ZDF90 (n = 6) |
| --- | --- | --- | --- |
| Urine Volume (ml/day) | 19 ± 3** | 175 ± 22 | 137 ± 24 |
| Urinary Albumin (mg/24 h) | 1.3 ± 0.4** | 44.7 ± 3.8 | 25.8 ± 4.8* |
| Total Urinary Protein (mg/24 h) | 22.2 ± 3.4** | 529.7 ± 122.7 | 176.4 ± 43.3** |
| Mean Kidney Weights (g) | 2.74 ± 0.05** | 4.79 ± 0.30 | 4.23 ± 0.27 |
| Relative Kidney Weights (g/kg) | 6.13 ± 0.14*$^8$ | 11.26 ± 0.43 | 12.23 ± 0.78 |

*$P < 0.05$ vs. ZDF rats;
**$P < 0.01$ vs. ZDF rats

Treatment of ZDF rats with LR-90 significantly prevented an increase in urinary albumin (42%, p<0.05) and total protein (67%, p<0.01), but not in urine output and kidney weights (Table 2). Reductions in both albumin and total protein excretion were strongly associated with attenuation of glomerulosclerosis and mesangial ECM accumulation (FIG. 1a,c,d), cortical tubule degeneration (FIG. 1b,e) and renal collagen deposition (FIG. 1b,f).

Renal TGF-β1, CTGF and ECM Proteins

Figure 3A:
FIG. 3. Renal immunohistochemical stainings for TGF-β1, CTGF and ECM proteins. Representative photomicrographs of immunostaining for (a) TGF-β1, (b) CTGF, (c) fibronectin and (d) collagen IV, showing the marked reduction of positive area staining for these growth factors and ECM proteins in ZDF rats treated with LR-90. Original magnification, ×320. ZDF90, LR-90-treated ZDF rats.
Figure 3B:
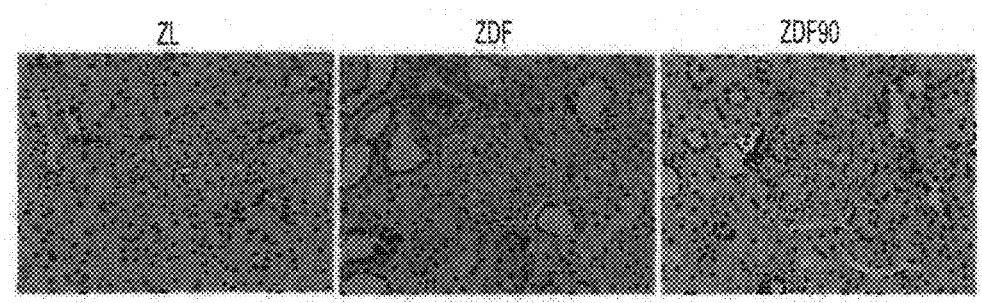
Figure 3C:
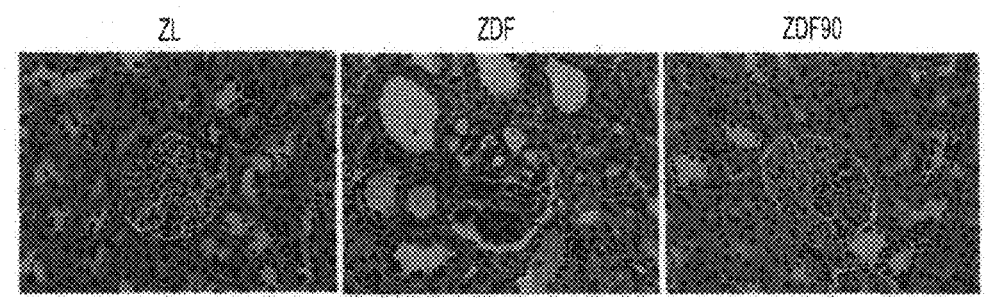
Figure 3D:
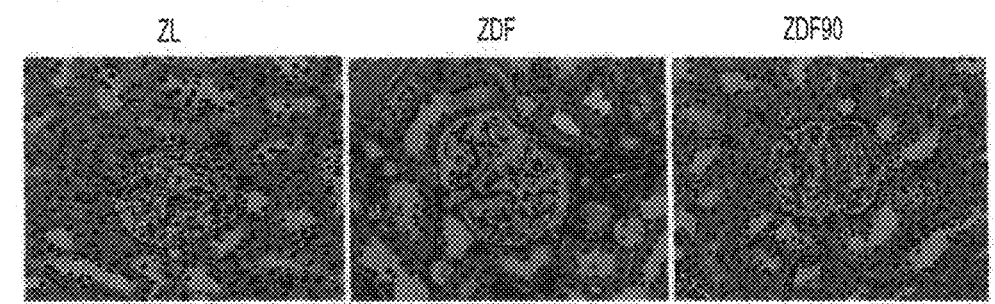

Both TGF-β1 and CTGF growth factors have been implicated in the pathogenesis of diabetic nephropathy, specifically in ECM accumulation and renal fibrosis. To examine whether LR-90 also affects the production of ECM proteins and fibrogenic cytokines, RT-PCR, Western blotting and immunostaining were performed. Tgfb1 and Ctgf mRNA (FIG. 2a,b) and protein (FIG. 2c-e) were significantly increased in kidneys of ZDF rats compared with ZL animals. Correspondingly, immunostaining for TGF-β1 was increased in the glomerular, epithelial and mesangial cells as well as in the tubulointerstitium of ZDF rats (FIG. 3a). CTGF immunostaining was also increased in ZDF rats, this being more prominent in the tubulointerstitial areas (FIG. 3b). Treatment with LR-90 significantly attenuated both mRNA expression and protein production of TGF-β1 and CTGF in the kidneys of ZDF animals (FIGS. 2a-e, 3a,b). Examination of fibronectin and collagen IV by immunohistochemical staining indicated that both ECM proteins could be lightly observed in the kidneys of ZL rats; fibronectin staining was mostly in the intraglomerular mesangium (FIG. 3c), with collagen IV weakly stained in the mesangium and tubulointerstitium (FIG. 3d). Both the intensity and area of fibronectin and collagen IV staining were dramatically increased in the ZDF rats compared with ZL animals, this increase being strongly associated with increased PAMS-positive materials in the glomeruli (FIG. 1a). Treatment with LR-90 markedly reduced the positive immunostaining for both ECM proteins to almost similar levels as those in ZL rats (FIG. 3c,d).

Renal MAPKs and NF-κB Activation

Figure 4A:
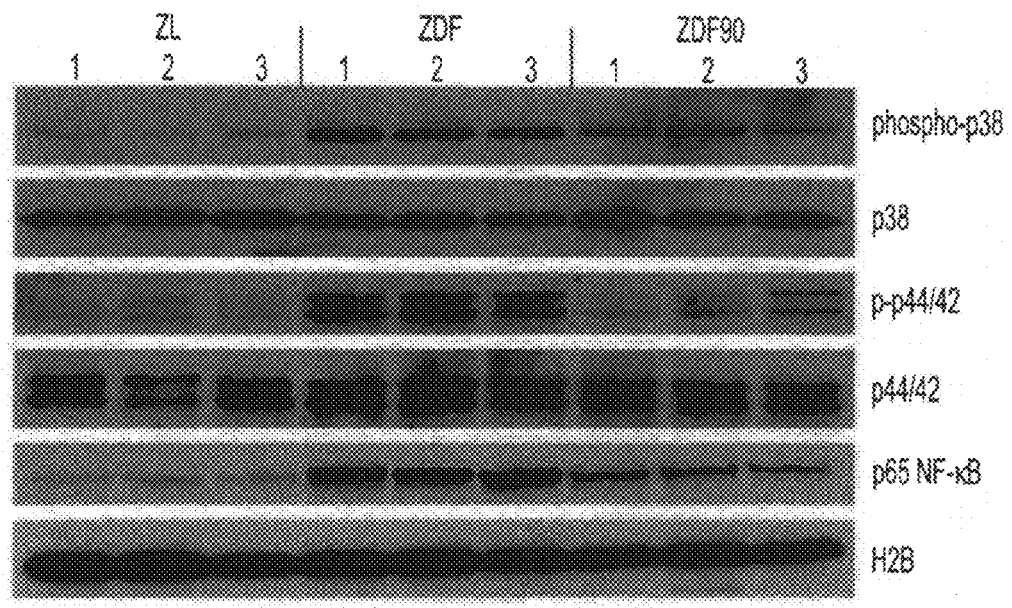
FIG. 4. LR-90 significantly attenuated renal MAPKs and NF-κB activation. Western blots (a) showing that the increased phosphorylation of p38 MAPK and p44/42 MAPK in the cortical lysates and activation of p65 subunit of NF-κB in the nucleus were significantly reduced by LR-90 treatment. Graph (b) shows the densitometric analyses (mean±SEM) of the ratio of p-p38 and p-p44/42 MAPK to total p38 MAPK and p44/42 MAPK, respectively and p65 to histone H2B. White bars, ZL; black bars, ZDF; chequered bars, ZDF90. *$p<0.05$, **$p<0.01$ vs ZDF (n=3). p, phospho; ZDF90, LR-90-treated ZDF rats.
Figure 4B:
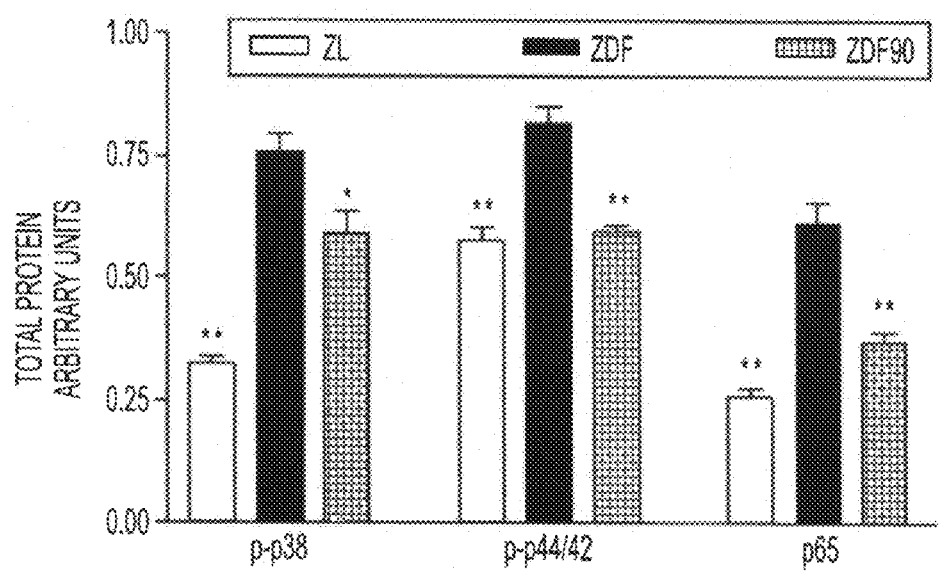

Pathways analyses have demonstrated that activation of MAPKs and NF-κB are key intracellular signals that play important roles in the progression of diabetic nephropathy, with the latter as important mediator of the inflammatory pathways [30]. We therefore analysed the activation of key growth and stress related MAPKs and the redox-sensitive transcription factor NF-κB in the cortical tissues of experimental rats using western blotting. Compared with ZL animals, ZDF rats exhibited robust activation of p38 and p44/42 MAPKs, as assessed by an increase in the levels of phosphorylation of their corresponding phosphorylated proteins. Similarly, activation of p65 subunit of NF-κB was 2.3-fold higher in kidneys of ZDF rats than in those of ZL rats. Treatment with LR-90 significantly attenuated the activation of p38 ($p<0.05$) and p44/42 ($p<0.01$) MAPKs, as well as NF-κB ($p<0.01$; FIG. 4a,b).

Plasma and Renal AGE and AGER

Circulating plasma CML-AGE concentration was increased 1.5-fold in ZDF rats, which was significantly attenuated by LR-90 treatment (22%, $p<0.01$; FIG. 5a). A significant correlation between plasma CML-AGE and albuminuria was observed ($r=0.82$, $p<0.0001$; FIG. 5b). Subsequent immunohistochemical analysis of CML-AGE formation in the renal cortex showed a marked increase in AGE staining in the glomeruli and the cortical tubules, as well as in interstitium (FIG. 5c). AGER immunostaining, primarily in the cortical tubules and interstitium, was also increased in the ZDF rats (FIG. 5d). This enhanced AGER staining was strongly associated with increased Ager expression (FIG. 5e). LR-90 treatment markedly abrogated both AGE accumulation and Ager mRNA and protein in kidney tissues of ZDF rats (FIG. 5a,c-e).

Kidney Lipid Peroxidation

Figure 6A:
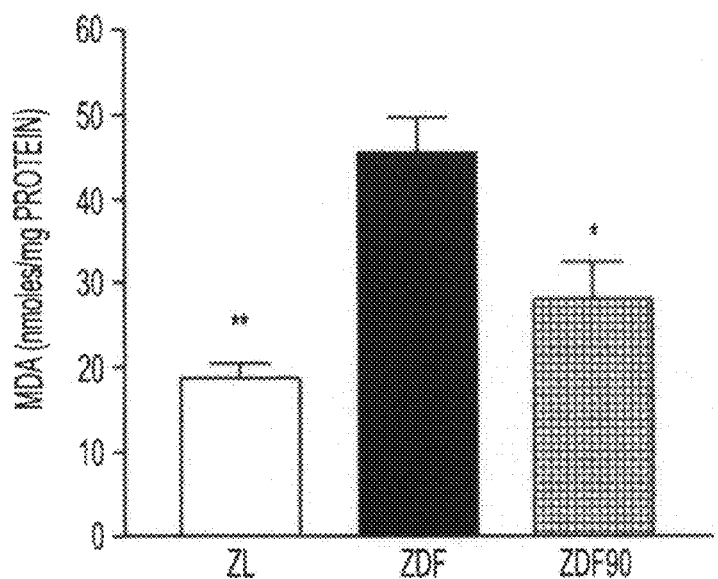
FIG. 6. LR-90 prevents renal lipidperoxidation. Kidney lipid peroxidation (a) was quantified by measuring malondialdehyde (MDA) in tissue homogenates using the thiobarbituric acid-reactive substances method. *$p<0.05$, **$p<0.01$ vs ZDF. b Correlation analysis showing strong association between kidney lipid peroxidation and urinary albumin excretion ($r=0.81$, $p<0.0001$ if data were merged from all three groups). White circles, ZL; black circles, ZDF; white squares, ZDF90. ZDF90, LR-90-treated ZDF rats.
Figure 6B:
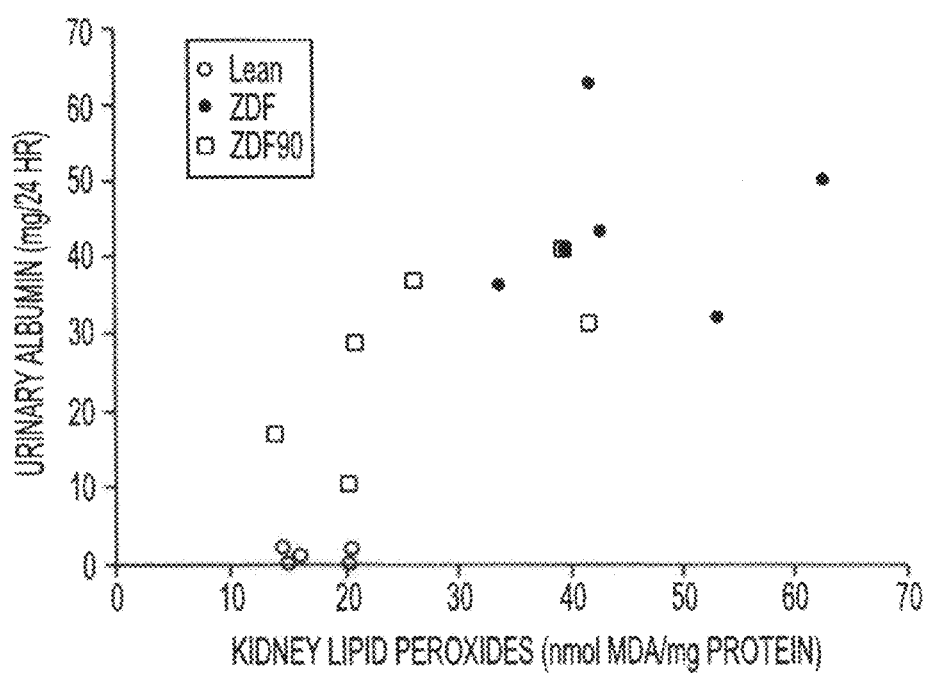

Renal tissue malondialdehyde concentrations were increased 2.5-fold in ZDF rats compared with lean rats (FIG. 6a), which correlated strongly with albumin excretion rates ($r=0.81$, $p<0.0001$; FIG. 6b). Treatment with LR-90 substantially reduced kidney lipid peroxidation in ZDF animals by almost 40% (FIG. 6a).

Discussion

Preventing or delaying the progression of diabetic nephropathy has been a major goal in biomedical research. Current therapeutic approaches such as ACE inhibitors and ARBs are clearly of value in reducing progression of established diabetic kidney disease [31]. However, the epidemic rise in the number of patients with end-stage renal disease due to diabetes continues, even though ACE inhibitors and ARBs are widely prescribed [32]. Developing innovative therapeutic alternatives for combating diabetic nephropathy, a comprehensive understanding of the pathophysiology of this disease would be beneficial.

The present Example demonstrates (in a rat model of type 2 diabetes), the possibility of preventing diabetic nephropathy using LR-90, a compound that was initially identified as an AGE inhibitor and has recently been shown to exhibit other properties, such as metal chelator, antioxidant, free radical scavenger, and anti-inflammatory [22-24]. Consistent with earlier studies on streptozotocin-diabetic rats [26], LR-90 significantly reduced albuminuria and prevented kidney damage in the ZDF rats by limiting glomerular and tubular injuries. These benefits occurred in the context of reduced renal AGE accumulation and AGER production, with modest, but not statistically significant effects on hyperglycaemia and the moderate increase in blood pressure characteristic of ZDF rats. Furthermore, LR-90 provided additional beneficial effects by lowering plasma lipids and preventing lipid peroxidation in renal tissues. These findings suggest that even in type 2 diabetes, where obesity and hyperglycaemia combined with dyslipidaemia, increased insulin resistance and hypertension result in enhanced actions of several risk factors for organ damage, LR-90 was able to attenuate renal injury by modulating several metabolic factors involved in the pathogenesis of diabetic nephropathy. More recently, the present inventors also observed similar renoprotective effects of LR-90 on db/db mice (S. Rahbar and J. L. Figarola, unpublished observations), further supporting the bioefficacy of this compound in preventing the development of type 2 diabetic nephropathy.

It has been suggested that diabetic nephropathy occurs as a result of interactions between metabolic and haemodynamic factors, which activate common pathways leading to increasing proteinuria, glomerulosclerosis and tubulointerstitial fibrosis [35]. The haemodynamic factors act independently or in concert with metabolic factors to activate intracellular second messengers such as protein kinase C and MAPKs, NF-κB and various growth factors, which work in a coordinated manner to promote increased production and deposition of ECM proteins such as collagen, fibronectin and laminin. ECM accumulation in the glomeruli and tubulointerstitial fibrosis have been considered to be principal hallmarks of diabetic nephropathy and result from an imbalance between signaling activities of the different growth factors involved in renal matrix homeostasis [36]. TGFβ-dependent and independent upregulation of CTGF and associated downstream signaling pathways appear to be important prosclerotic and profibrotic events in ECM regulation, as both TGF-β1 and CTGF have been demonstrated to contribute to the pathology of diabetic nephropathy in studies with experimental and human diabetes, as well as with glomerular cells [37, 38]. Production of these growth factors has been previously shown to be regulated by AGE-AGER activation [39, 40]. In the present Example, ECM accumulation and renal fibrosis, along with increased Tgfb1 and Ctgf mRNA expression and protein production, were observed in ZDF rats, results that were significantly attenuated by LR-90 treatment. Moreover, glomerular and tubular injuries were also minimised by the compound, with concomitant improvement in renal function in ZDF rats. Taken together, these results indicate that aside from inhibiting circulating and tissue AGE accumulation and AGER activation in the diabetic kidney, LR-90 treatment may also influence various intracellular signalling pathways associated with mesangial ECM accumulation and tubulointerstitial fibrosis.

Pathways analyses have demonstrated that MAPK activation, including p38 and p44/42 MAPK signaling pathways, are profibrotic contributors to diabetic nephropathy [41, 42]. These intracellular signals have also been shown to be partly mediated by AGE-AGER interaction and subsequent oxidant stress [43, 44]. Thus, in further elucidating possible mechanisms of the pharmacological effects of LR-90 against renal fibrosis in ZDF rats, we also demonstrated that LR-90 downregulated the activation of MAPKs p38 and p44/42 in renal cortex. Furthermore, we also showed that LR-90 inhibited the activation of the redox-sensitive transcription factor NF-κB, suggesting that LR-90 may also mediate the inflammatory reactions and associated gene expression of various cytokines involved in the pathogenesis of diabetic nephropathy. Our recent studies in monocytes further confirm this action of LR-90, where suppression of NF-κB activation by the compound was associated with its antioxidant activities against NADPH-mediated superoxide generation [26]. Indeed, accumulating evidence in vitro suggests that the response of mesangial cells, as well as tubular epithelial cells to hyperglycaemia is driven primarily by reactive oxygen species [36, 45]. More recent studies on ZDF rats seem to support this concept, arguing that oxidative stress is precedent to renal injury in this animal model [15, 46]. Although we only performed limited tests to evaluate the oxidant status of ZDF rats treated with LR-90 (i.e. kidney lipid peroxidation), it is logical, on the basis of: (1) our previous studies with monocytes [26]; (2) the effects of LR-90 on renal nitrotyrosine in streptozotocin-diabetic rats [24]; and (3) our observation that the compound also attenuated the increased kidney expression of Cybb, the gene encoding for the gp91phox subunit of NADPH (data not shown), to assume that the LR-90 could also prevent renal oxidative stress in this animal model.

In addition to hyperglycaemia, untreated ZDF rats exhibited severe hyperlipidaemia and increased lipid peroxidation. Interestingly, we found the latter, measured as malondialdehyde in tissues, correlated well with urinary albumin excretion ($r=0.81$, $p<0.0001$). Malondialdehyde has been widely recognised as an important marker of lipid peroxidation and has been shown to correlate strongly with the degree of renal damage in experimental and human diabetic nephropathy [47]. Experimental evidence linking hyperlipidaemia to renal injury and progression of renal fibrogenesis has been well documented; lipids can modulate the progression of chronic renal diseases and may even be primary factors in the pathogenesis of renal tissue injury [48, 49]. Additionally, the synergistic effects of hyperlipidaemia and diabetes on the development of renal injury have been recently observed in several animal models. In Apoe knockout mice, hyperlipidaemic animals with diabetes displayed a more extensive and severe degree of renal glomerular and tubulointerstitial injury as well as higher levels of urinary albumin excretion when compared with normolipidaemic diabetic animals [50]. Similarly, in obesity prone and spontaneously hypertensive hybrid rat models (SHHF/Gmi-fa×LA/N-fa), the development of glomerulosclerosis and interstitial fibrosis was dependent on lipoxidation, as without hypercholesterolaemia, glycoxidation per se was not nephrotoxic [51]. Nonetheless, it remains unclear whether hyperglycaemia-driven AGE formation or lipids have a greater impact on the development of diabetic nephropathy in this animal model. Earlier studies in ZDF rats demonstrated that both elevated triacylglycerol and cholesterol, and progressive accumulation of lipids and their peroxidation products in the glomeruli and tubulointerstitium predate the development of glomerular and tubular damage in ZDF rats [14, 15], suggesting that hyperlipidaemia, in concert with hyperglycaemia, may be responsible for the increased oxidative stress and initiation of injury in the kidneys of these animals. Thus, the ability of LR-90 to lower plasma lipids, as well as preventing the accumulation of lipid peroxidation products in the kidney as demonstrated in the present studies, may have contributed to some extent to its renoprotective effects, independently of its inhibitory effects on AGE formation and AGER activation.

The present Examples therefore demonstrates that LR-90 retards the development of nephropathy in ZDF rats, concomitantly with marked inhibition of AGE formation and subsequent AGER production, a reduction in plasma lipids and kidney peroxides, and downregulation of expression of prosclerotic growth factors, matrix proteins and downstream intracellular signals such as p38 and p44/42 MAPKs, which are involved in glomerulosclerosis and renal fibrosis. Additionally, LR-90 downregulated activation of the inflammatory transcription factor NF-κB. While the mechanisms by which LR-90 exerts its protective effects on the diabetic kidney are still not fully resolved, the present Example is consistent with the proposed pleiotrophic effects of LR-90 as an AGE inhibitor, antioxidant, antifibrotic, hypolipidaemic and anti-inflammatory agent.

Example 2

The present Example presents the results of an investigation of the effects of LR-90, an inhibitor of AGE/ALE formation, in male Zucker diabetic fatty rats (ZDF, fa/fa) fed with Purina 5008 diet until 40 weeks of age, and their hetorozygous lean littermates (ZDF fa/+) as non-hyperglycemic controls. LR-90 at 50 mg/L of drinking water was given to a subgroup of ZDF rats after the rats developed spontaneous diabetes at 13 weeks of age. At 40 weeks of age, and before killing the animals, their weight was measured; $HbA_1c$, plasma glucose, insulin, triglycerides, cholesterol, CRP and urinary albumin and creatinine concentrations were measured. After euthanizing all animals, organs such as the kidneys, eyeballs, liver, heart, aortae and pancreas were dissected and subjected to immunohistochemical staining, RT-PCR, Western blotting and microscopy.

Results

Table 3 shows the metabolic characteristics of the lean, ZDF and LR-90 treated ZDF rats at 40 weeks of age. (Table 3 also includes data generated with respect to LR-102). As expected, ZDF rats were hyperglycemic and hyperlipidemic compared with lean rats. Treatment of ZDF rats with LR-90 had no effect on hyperglycemia, but significantly reduced hyperlipidemia in these animals. The inflammatory marker C-reactive protein (CRP) was also elevated in ZDF rats relative to the lean rats and treatment with LR-90 attenuated this increase in CRP levels.

TABLE 3

Metabolic Data (Mean ± SEM)

| | Lean Control n = 6 | ZDF Control n = 6 | ZDF + LR-90 n = 6 | ZDF + LR-102 n = 4 |
|---|---|---|---|---|
| Plasma glucose (mmol/dL) | 9.6 ± 0.5 | 29.6 ± 1.3* | 25.0 ± 2.3 | 29.8 ± 3.2 |
| Plasma insulin, RIA (ng/ml) | 0.23 ± 0.02 | 1.12 ± .019* | 0.63 ± 0.04** | 0.65 ± 0.10** |
| Plasma insulin, ELISA (ng/ml) | 0.37 ± 0.06 | 1.18 ± 0.17* | 0.64 ± 0.10** | 0.68 ± 0.10** |
| HbA1c (%) | 1.25 ± 0.03 | 2.70 ± 0.17* | 2.89 ± 0.07 | 2.80 ± 0.12 |
| Triglycerides (mg/dL) | 165 ± 14 | 858 ± 184* | 384 ± 51** | 536 ± 63 |
| Cholesterol (mg/dL) | 97 ± 6 | 346 ± 35* | 244 ± 13** | 290 ± 35 |
| Body Weight (g) | 448 ± 5 | 425 ± 18 | 347 ± 32 | 359 ± 30 |
| Plasma CRP (mg/mL) | 0.54 ± 0.02 | 0.84 ± 0.04* | 0.58 ± 0.09** | 0.77 ± 0.05 |
| Urinary Albumin (mg/24 h) | 1.3 ± 0.4 | 44.6 ± 3.8* | 27.8 ± 4.8*** | 35.4 ± 15.8 |

*P < 0.01 vs. lean;
**P < 0.05 vs. ZDF;
***P < 0.01 vs. ZDF

Figure 7:
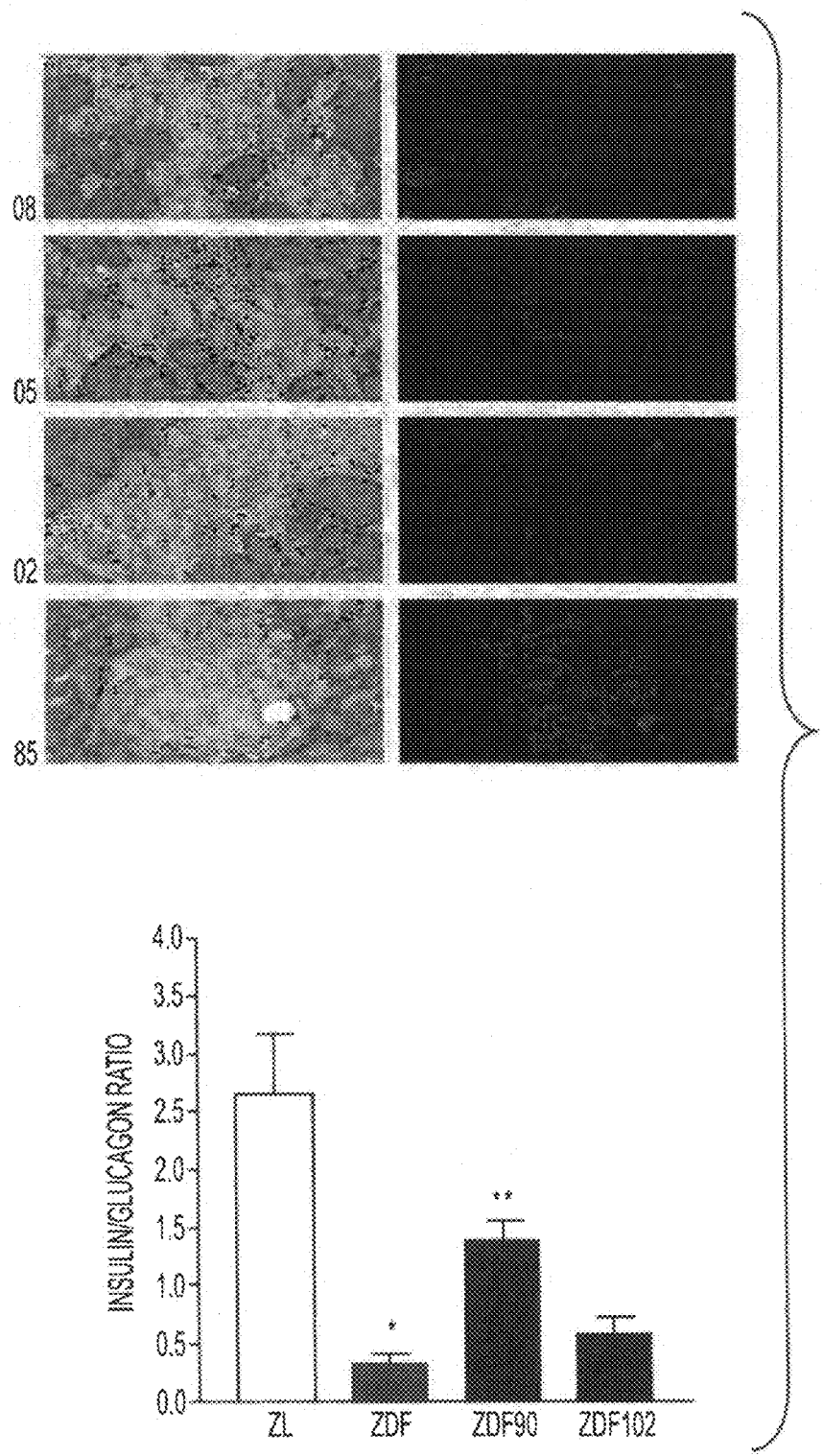
FIG. 7. Immunohistochemical analysis and quantification of islet cells. ZDF GM fa/fa rats and lean control rats were fed with high fat diet for 30 weeks and received either nothing or LR-90 or LR-102 in their drinking water. Pancreatic sections from various groups of animals were stained with anti-insulin antibody or anti-glucagon antibody. A. Representative images with the overlay of the insulin (green) and glucagon (red staining). Left panel shows the H&E staining of the pancreatic tissue and right panel is overlays of images from staining with anti-insulin antibody and anti-glucagon antibody. B. Insulin-positive β-cell-to-glucagon-ratio was also measured from these images. 08=lean non-diabetic animal; 05=ZDF diabetic control; 02 ZDF+LR-90; and 85=ZDF+LR-102. *$P<0.01$ vs. lean, **$P<0.01$ vs. ZDF.
Figure 8:
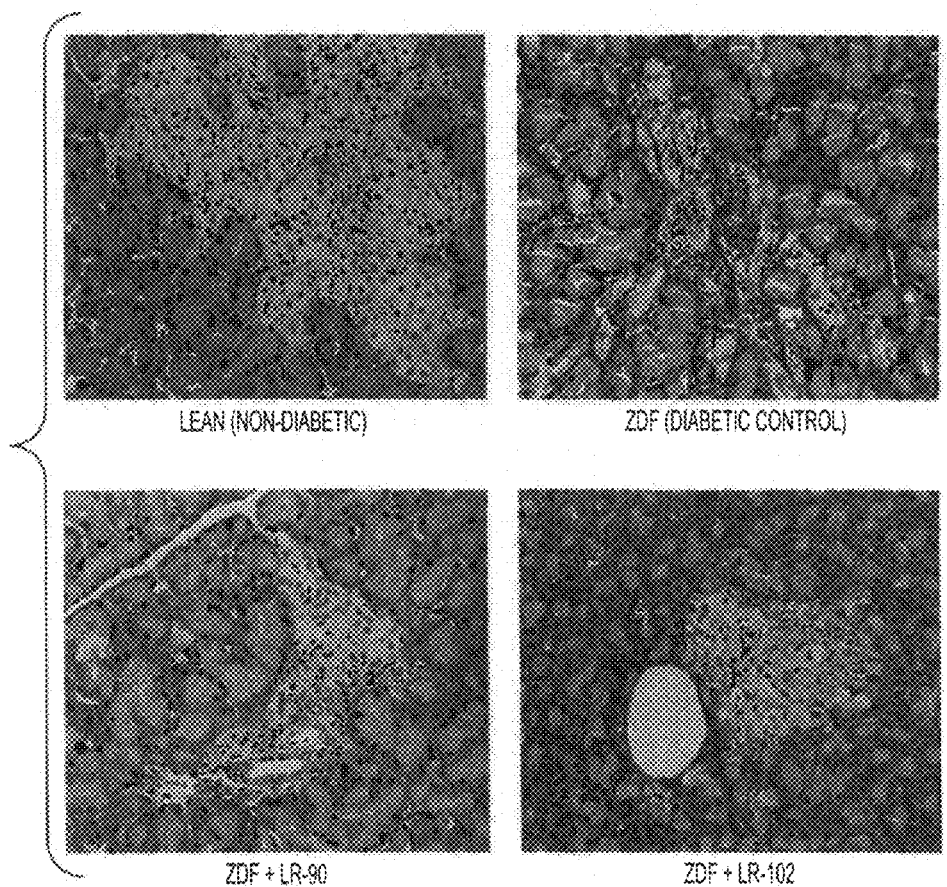
FIG. 8. Periodic acid methenamine silver (PAMS) staining of pancreatic tissues. Sections from cryopreserved pancreas of each group of animals on the study were stained with PAMS and examined under light microscopy. Upper left panel shows normal structure of islet (left) and deranged, damaged islets, with accumulation of fibrosclerotic tissues in the islets in ZDF diabetic control animals (upper right panel). Lower panel demonstrates amelioration of the islets from the animal groups treated with LR-90 (left), and LR-102 (right).

To examine whether LR-90 affects the pancreas and insulin secretion, plasma insulin was measured using both ELISA and RIA methods. As shown in Table 3, plasma insulin levels (measured by ELISA and RIA) were also elevated in ZDF rats compared to the lean rats. In addition, immunohistochemical analysis and quantification of islet cells in the pancreatic tissues demonstrated decreased insulin staining in ZDF rats compared with lean rats (FIG. 7), which was associated with deranged, damaged islets, and accumulation of fibrosclerotic tissues in the islets (FIG. 8). ZDF rats given LR-90 had reduced levels of plasma insulin (Table 3), and had significantly higher number of undamaged insulin-secreting islet cells in the pancreas (FIGS. 7 and 8). Taken together, these results suggest that LR-90 could prevent development of insulin-resistance in this model of Type 2 diabetes.

Figure 9A:
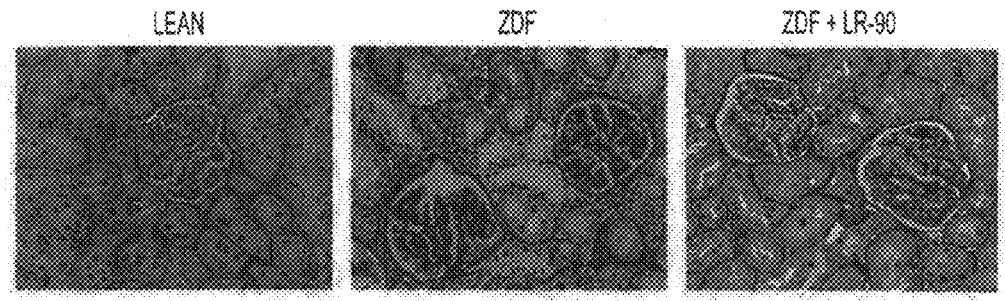
FIG. 9. Representative photomicrographs of immunohistochemicals stainings of kidney tissues. A. Periodic Acid-Metheamine Silver (PAMS); B, Masson'S Trichrome; C, AGE; and D, RAGE stainings of kidneys from lean, ZDF and LR-90 treated ZDF rats.
Figure 9B:
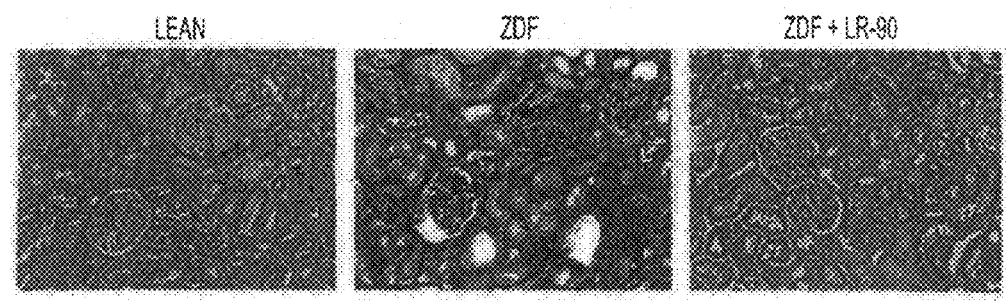
Figure 9C:
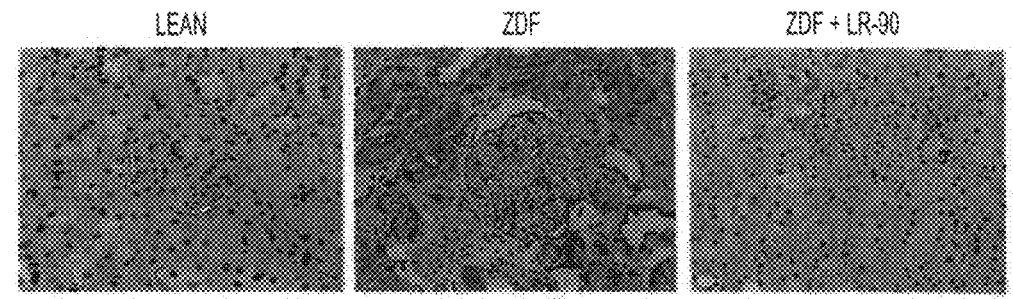
Figure 9D:
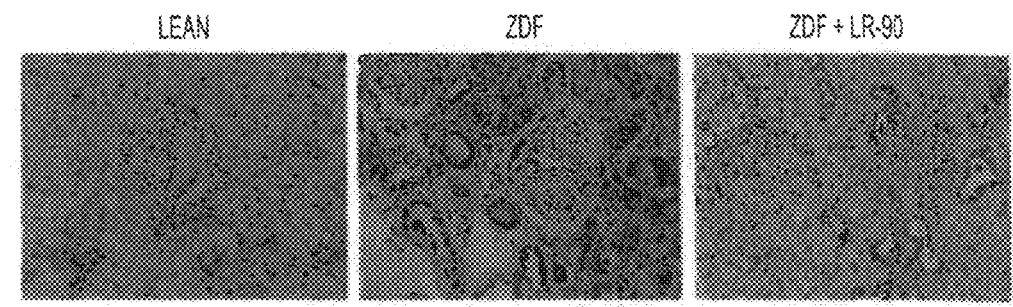
Figure 10:
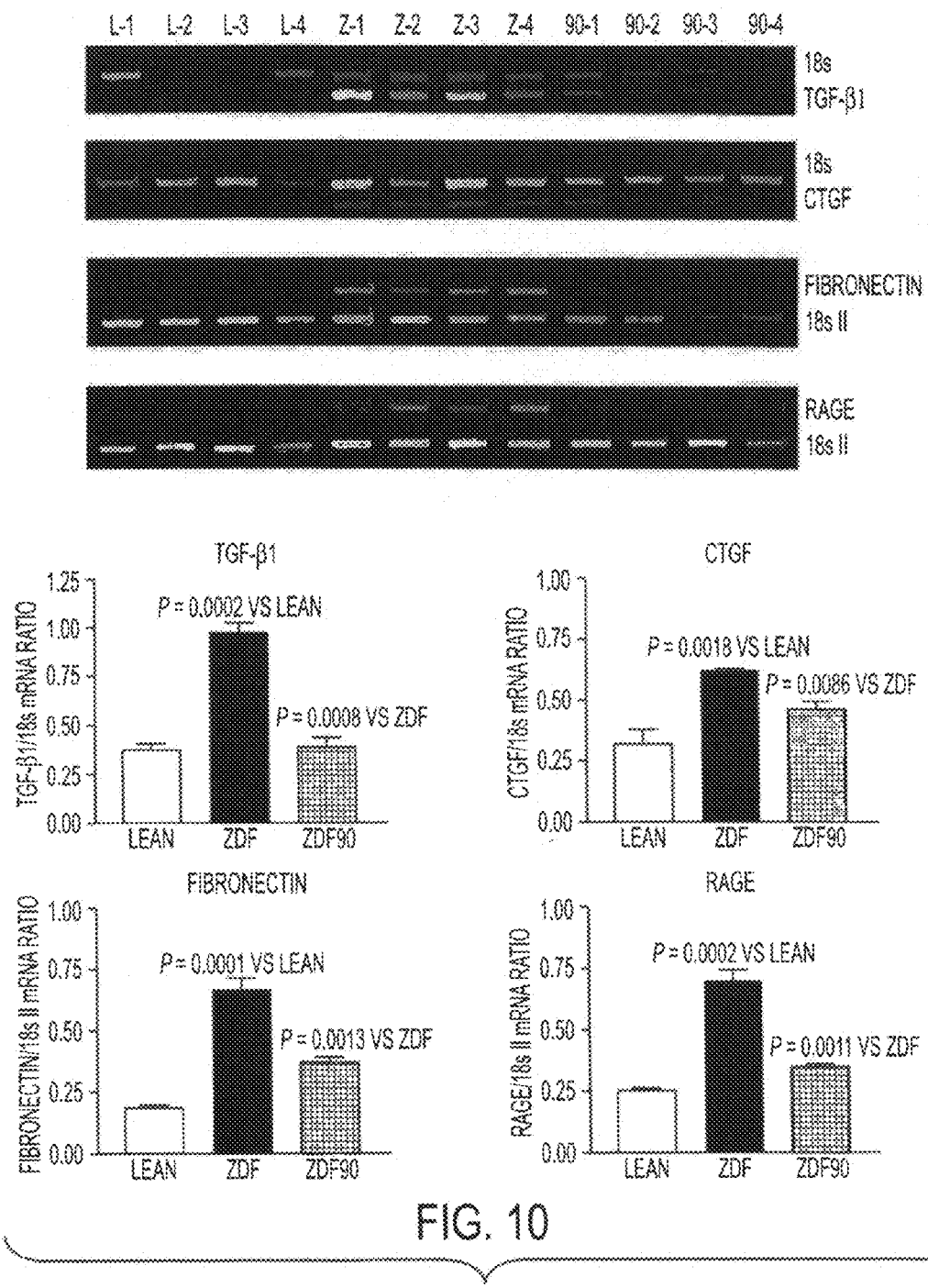
FIG. 10. mRNA expression of TGF-B1, CTGF, fibronectin and RAGE in the kidney cortex. Renal cortices from each treatment group were analyzed by for TGF-B1, CTGF, fibronectin and RAGE gene expression by RT-PCR. A. Representative gel profiles; B, Quantitative results of band densities. 18s/18 sII were used as internal controls.
Figure 11:
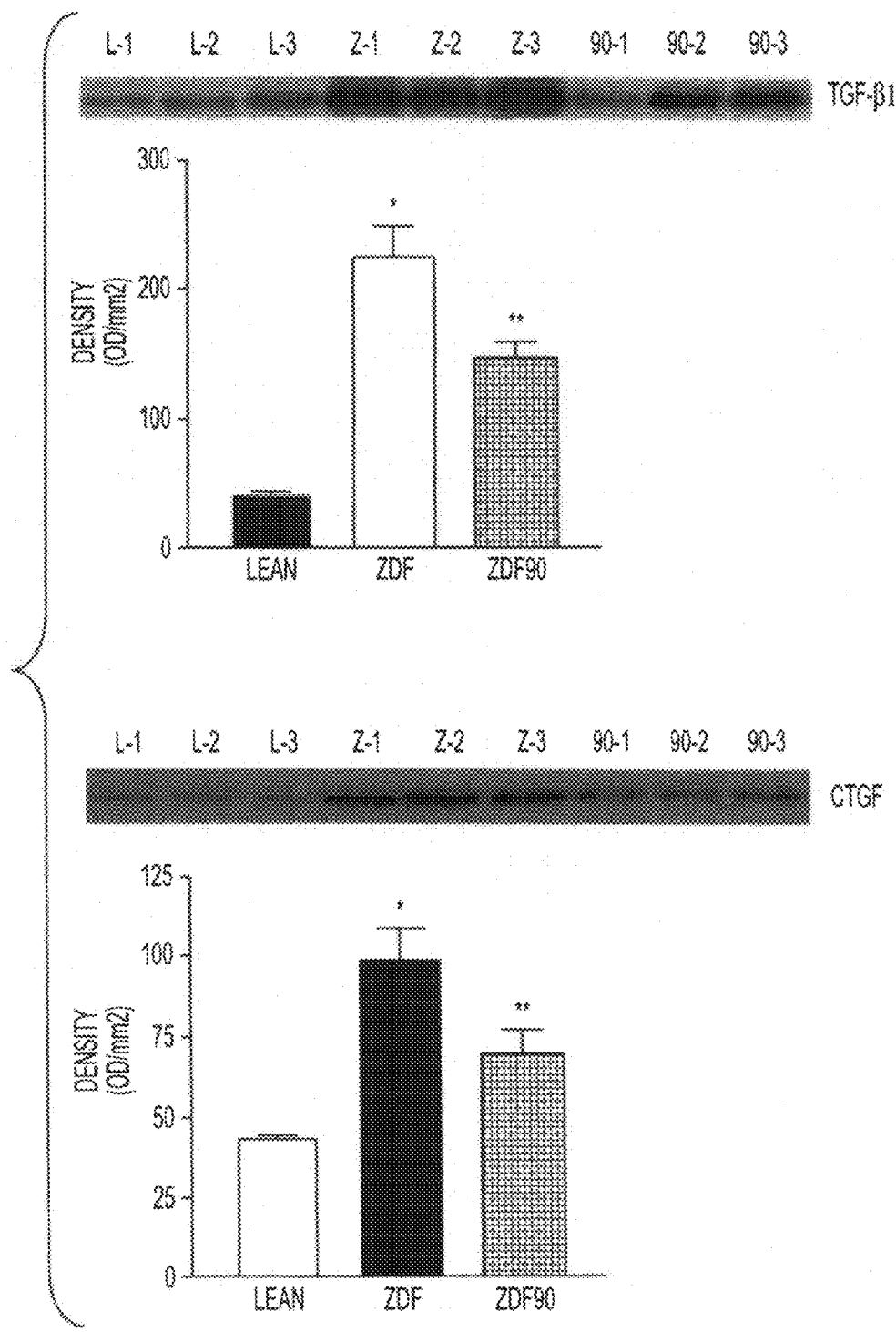
FIG. 11. Protein expression of TGF-B1 and CTGF in the kidney cortex. Renal cortices from each treatment group were analyzed by for TGF-B1 and CTGF protein expression by Western blotting and immunostaining with specific antibodies. Representative gel profiles and densiitometric quantitation of protein bands. *P<0.01 vs. lean, **P<0.01 vs. ZDF FIG. 12. Representative immunohistochemical staining for TGF-B1 and CTGF in the kidney cortex. Renal cortices from each treatment group were probed with specific antibodies against TGF-β1 and CTGF.
Figure 12:
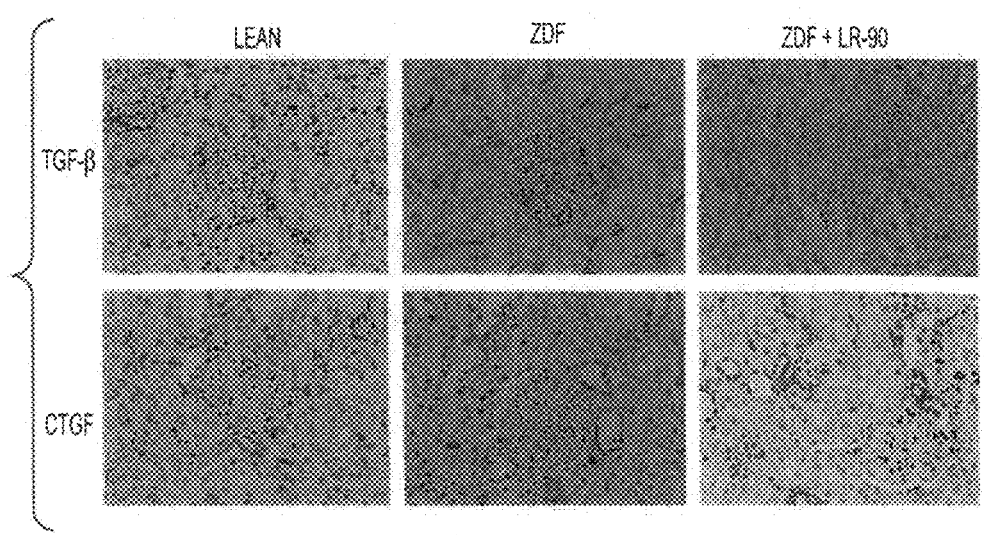

We have demonstrated earlier that LR-90 can prevent diabetic complications in experimental Type 1 diabetes, including diabetes nephropathy (24). In the present Example, we have also observed the same renoprotective effects of the drug in ZDF animals. LR-90 significantly corrected albuminuria (Table 3) and prevented glomerulosclerosis, tubular degeneration and collagen deposition (FIGS. 9a and b), concomitant with reduced renal AGE and RAGE accumulation in the kidney of ZDF rats (FIGS. 9c and d). In addition, the mRNA expression of TGF-β1 and CTGF, two growth factors associated with fibrosis and ECM accumulation in diabetic nephropathy, as well as fibronectin and RAGE, were significantly increased in ZDF rats (FIG. 10). Correspondingly, TGF-β1 and CTGF protein expression, measured by Western blotting and immunostaining, were also significantly increased (FIGS. 11 and 12). Treatment with LR-90 significantly attenuated TGF-β1 and CTGF gene and protein expression, as well as fibronectin and RAGE mRNA in the kidneys of ZDF rats (FIGS. 10, 11, and 12).

Figure 13A:
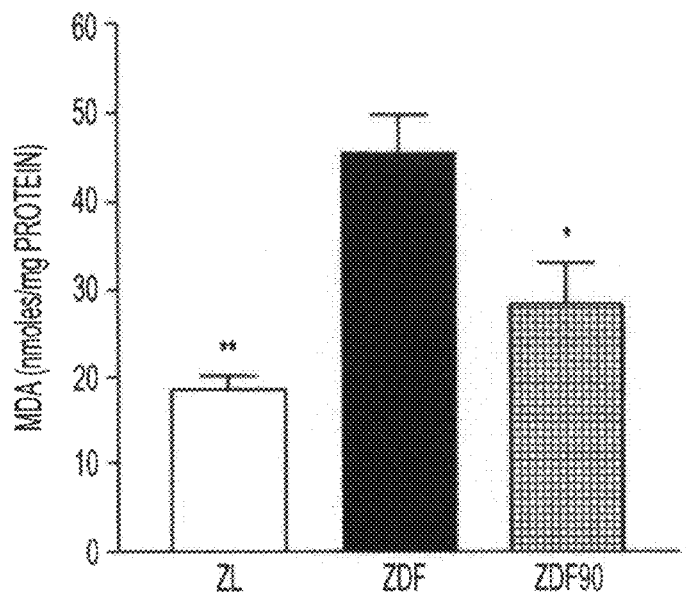
FIG. 13. Effect of LR-90 on kidney lipid peroxidaton. A. Kidney lipid peroxides were analyzed by measuring malondialdehyde (MDA) in tissue homogenates using the TBARS method. B. Correlation of lipid peroxidation with urinary albumin excretion rates. *P<0.05 vs. ZDF, **P<0.01 vs. ZDF.
Figure 13B:
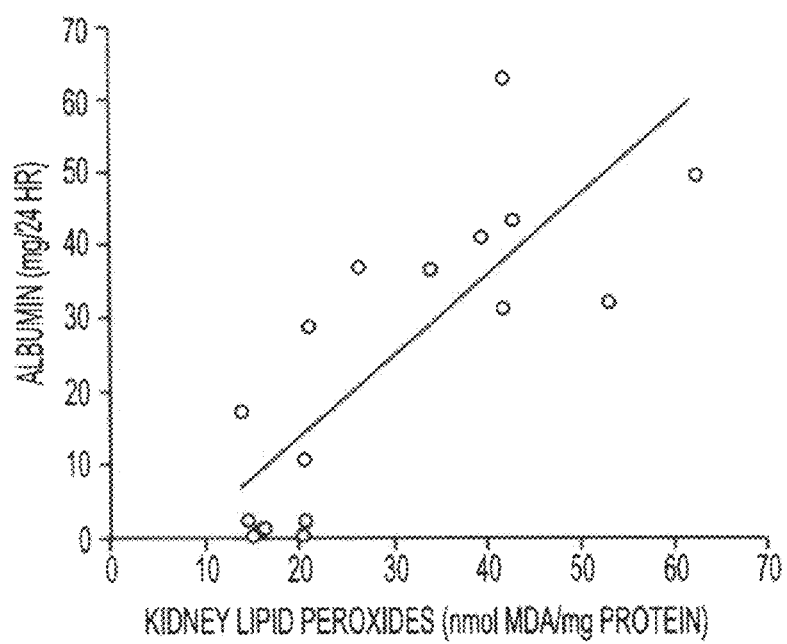

In addition to hyperglycemia, the untreated ZDF rats exhibited severe hyperlipidemia and increased renal lipid peroxidation. Renal tissue MDA concentrations were increased ~2.5 fold in ZDF rats compared with lean rats (FIG. 13a), which correlated strongly with urinary albumin excretion rates ($r^2$=0.65, P<0.0001, FIG. 13b). Treatment with LR-90 substantially reduced kidney lipid peroxidation in ZDF animals by almost 40% (FIG. 11a). Thus, the ability of LR-90 to lower plasma lipids, as well as preventing the accumulation of lipid peroxidation products in the kidney as demonstrated in the present studies, may have contributed to some extent, to its renoprotective effects independent of its effects on hyperglycemia and AGE formation.

Example 3

Figure 14:
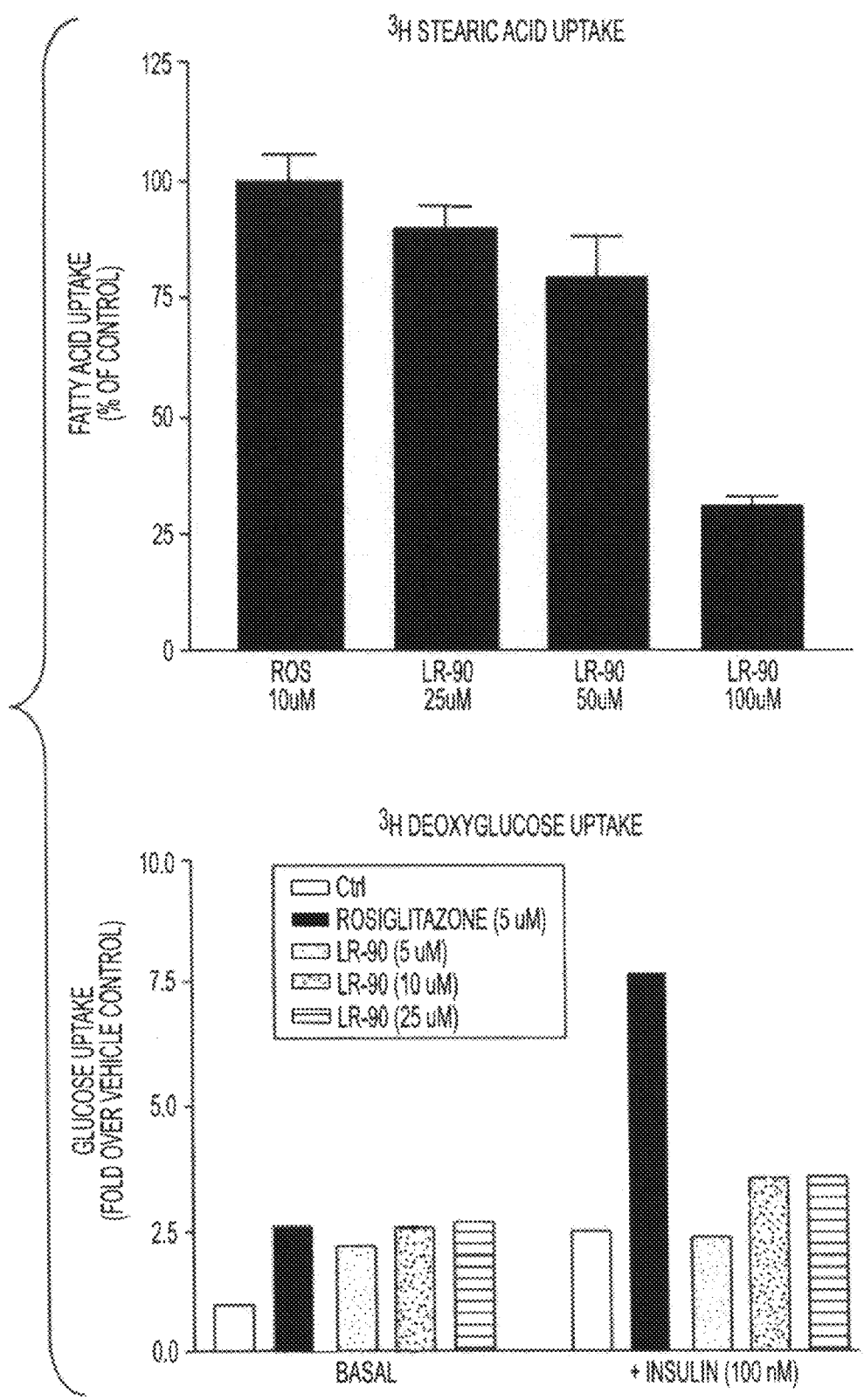
FIG. 14. Effect of LR-90 on 3T3 adipocytes. Tissue culture data on 3T3 adipocytes, showing free fatty acid (FFA) uptake and glucose uptake improvements upon contact with LR-90.

The present Example, with reference to FIG. 14, provides tissue culture data on 3T3 adipocytes, showing free fatty acid (FFA) uptake and glucose uptake improvements upon contact with LR-90.

REFERENCES

1. Friedman E A, Friedman A L (2007) Is there really good news about pandemic diabetic nephropathy? Nephrol Dial Transplant 22:681-683
2. Rossing P (2006) Diabetic nephropathy: worldwide epidemic and effects of current treatment on natural history. Curr Diab Rep 6:479-483
3. Lehmann R, Schleicher E D, Lehmann R, Schleicher E D (2000) Molecular mechanism of diabetic nephropathy. Clin Chim Acta 297:135-144
4. Raptis A E, Viberti G (2001) Pathogenesis of diabetic nephropathy. Exp Clin Endocrinol Diabetes 109(Suppl 2):S424-S437
5. Thomas M C, Forbes J M, Cooper M E (2005) Advanced glycation end products and diabetic nephropathy. Am J Ther 12:562-572
6. Bohlender J M, Franke S, Stein G, Wolf G (2005) Advanced glycation end products and the kidney. Am J Physiol 289: F645-F659
7. Horie K, Miyata T, Maeda K et al (1997) Immunohistochemical colocalization of glycoxidation products and lipid peroxidation products in diabetic renal glomerular lesions. J Clin Invest 100:2995-3004
8. Tanji N, Markowitz G S, Fu C et al (2000) Expression of advanced glycation end products and their cellular receptor RAGE in diabetic nephropathy and nondiabetic renal disease. J Am Soc Nephrol 11:1656-1666
9. Jensen L J, Ostergaard J, Flyvbjerg A (2005) AGE-RAGE and AGE cross-link interaction: important players in the pathogenesis of diabetic kidney disease. Horm Metab Res 37(Suppl
10. Tan A L, Forbes J M, Cooper M E (2007) AGE, RAGE, and ROS in diabetic nephropathy. Semin Nephrol 27:130-143
11. Peterson R G Shaw W N, Neel M A et al (1990) Zucker diabetic fatty as a model for non-insulin dependent diabetes mellitus. ILAR News 32:16-19
12. Kasiske B L, O'Donnell M P, Keane W F (1992) The Zucker rat model of obesity, insulin resistance, hyperlipidemia, and renal injury. Hypertension 19(Suppl 1):1110-1115
13. Vora J P, Zimsen S M, Houghton D C, Anderson S (1996) Evolution of metabolic and renal changes in the ZDF/Drt-fa rat model of type II diabetes. J Am Soc Nephrol 7:113-117
14. Coimbra T M, Janssen U, Grone H J et al (2000) Early events leading to renal injury in obese Zucker (fatty) rats with type II diabetes. Kidney Int 571:167-182
15. Chander P N, Gealekman O, Brodsky S V et al (2004) Nephropathy in Zucker diabetic fat rat is associated with oxidative and nitrosative stress: prevention by chronic therapy with a peroxynitrite scavenger ebselen. J Am Soc Nephrol 15:2391-2403
16. McCarthy K J, Routh R E, Shaw W, Walsh K, Welbourne T C, Johnson J H (2000) Troglitazone halts diabetic glomerulosclerosis by blockade of mesangial expansion. Kidney Int
17. Baylis C, Atzpodien E A, Freshour G, Engels K (2003) Peroxisome proliferator-activated receptor γ agonist provides superior renal protection versus angiotensin-converting enzyme inhibition in a rat model of type 2 diabetes with obesity. J Pharmacol Exp Ther 307:854-860
18. Mizuno M, Sada T, Kato M, Koike H (2002) Renoprotective effects of blockade of angiotensin II AT1 receptors in an animal model of type 2 diabetes. Hypertens Res 25:271-278
19. Wihler C, Schafer S, Schmid K et al (2005) Renal accumulation and clearance of advanced glycation end-products in type 2 diabetic nephropathy: effect of angiotensin-converting enzyme and vasopeptidase inhibition. Diabetologia 48:1645-1653
20. Schäfer S, Linz W, Vollert H et al (2004) The vasopeptidase inhibitor AVE7688 ameliorates type 2 diabetic nephropathy. Diabetologia 47:98-103
21. Schrijvers B F, Flyvbjerg A, Tilton R G et al (2006) A neutralizing VEGF antibody prevents glomerular hypertrophy in a model of obese type 2 diabetes, the Zucker diabetic fatty rat. Nephrol Dial Transplant 21:324-329
22. Rahbar S, Figarola J L (2003) Novel inhibitors of advanced glycation endproducts. Arch Biochem Biophys 419:63-79
23. Rahbar S (2007) Novel inhibitors of glycation and AGE formation. Cell Biochem Biophys
24. Figarola J L, Scott S, Loera S et al (2003) LR-90, a novel advanced glycation endproduct inhibitor, prevents progression of diabetic nephropathy in streptozotocin-diabetic rats. Diabetologia 46:1140-1152
25. Figarola J L, Rahbar S, Scott S et al (2005) Prevention of early renal disease, dyslipidemia and lipid peroxidation in STZ-diabetic rats by LR-9 and LR-74, novel AGE inhibitors. Diabetes Metab Res Rev 21:533-544
26. Figarola J L, Shanmugam N, Natarajan R, Rahbar S (2007) Antiinflammatory effects of the advanced glycation end product inhibitor LR-90 in human monocytes. Diabetes 56:647-655
27. Wilkinson-Berka J L, Kelly D J, Koerner S M et al (2002) ALT-946 and aminoguanidine, inhibitors of advanced glycation, improve severe nephropathy in the diabetic transgenic (mREN-2) rat. Diabetes 51:3283-3289
28. Ohga S, Shikata K, Yozai K et al (2006) Thiazolidinedione ameliorates renal injury in experimental diabetic rats through anti-inflammatory effects mediated by inhibition of NF-κB activation. Am J Physiol 292:F1141-F1150
29. Reckelhoff J F, Kanji V, Racusen L C et al (1998) Vitamin E ameliorates enhanced renal lipid peroxidation and accumulation of F2-isoprostanes in aging kidneys. Am J Physiol 274:R767-R774
30. Chuang L, Guh J (2001) Extracellular signals and intracellular pathways in diabetic nephropathy. Nephrology 6:165-172
31. Thomas M C, Atkins R C (2006) Blood pressure lowering for the prevention and treatment of diabetic kidney disease. Drugs 66:2213-2234
32. Song J H, Cha S H, Hong S B, Kim D H (2006) Dual blockade of the rennin-angiotensin system with angiotensin-converting enzyme inhibitors and angiotensin TI receptor blockers in chronic kidney disease. J Hypertens Suppl 24:S101-S106
33. Davis B J, Forbes J M, Thomas M C et al (2004) Superior renoprotective effects of combination therapy with ACE and AGE inhibition in the diabetic spontaneously hypertensive rat. Diabetologia 47:89-97
34. Wu Y G, Lin H, Qian H et al (2006) Renoprotective effects of combination of angiotensin converting enzyme inhibitor with mycophenolate mofetil in diabetic rats. Inflamm Res 55:192-R199
35. Forbes J M, Fukami K, Cooper M E (2007) Diabetic nephropathy: where hemodynamics meets metabolism. Exp Clin Endocrinol Diabetes 115:69-84
36. Mason R M, Wahab N A (2003) Extracellular matrix metabolism in diabetic nephropathy. J Am Soc Nephrol 14:1358-1373
37. Reeves W B, Andreoli T E (2000) Transforming growth factor beta contributes to progressive diabetic nephropathy. Proc Natl Acad Sci USA 97:7667-7669
38. Wahab N A, Yevdokimova N, Weston B S et al (2001) Role of connective tissue growth factor in the pathogenesis of diabetic nephropathy. Biochem J 359:77-87
39. Pugliese G, Pricci F, Romeo G et al (1997) Upregulation of mesangial growth factor and extracellular matrix synthesis by advanced glycation end products via a receptor-mediated mechanism. Diabetes 46:1881-1887
40. Zhou G, Li C, Cai L (2004) Advanced glycation end-products induce connective tissue growth factor-mediated renal fibrosis predominantly through transforming growth factor β-independent pathway. Am J Pathol 165:2033-2043
41. Crean J K, Finlay D, Murphy M et al (2002) The role of p42/44 MAPK and protein kinase B in connective tissue growth factor induced extracellular matrix protein production, cell migration, and actin cytoskeletal rearrangement in human mesangial cells. J Biol Chem Nov
42. Fujita H, Omori S, Ishikura K et al (2004) ERK and p38 mediate high-glucose-induced hypertrophy and TGF-β expression in renal tubular cells. Am J Physiol 286:F120-F126
43. Zill H, Bek S, Hofmann T et al (2003) RAGE-mediated MAPK activation by food-derived AGE and non-AGE products. Biochem Biophys Res Commun 300:311-315
44. Yeh C H, Sturgis L, Haidacher J et al (2001) Requirement for p38 and p44/p42 mitogen-activated protein kinases in RAGE-mediated nuclear factor-kappaB transcriptional activation and cytokine secretion. Diabetes 50:1495-1504
45. Lee H B, Yu M R, Yang Y, Jiang Z, Ha H (2003) Reactive oxygen species-regulated signaling pathways in diabetic nephropathy. J Am Soc Nephrol 14(Suppl 3):S241-S245
46. Suzaki Y, Ozawa Y, Kobori H (2006) Intrarenal oxidative stress and augmented angiotensinogen are precedent to renal injury in Zucker diabetic fatty rats. Int J Biol Sci 3:40-46
47. Chang J M, Kuo M C, Kuo H T et al (2005) Increased glomerular and extracellular malondialdehyde levels in patients and rats with diabetic nephropathy. J Lab Clin Med 146:210-R215
48. Abrass C K (2004) Cellular lipid metabolism and the role of lipids in progressive renal disease. Am J Nephrol 24:46-53
49. Rosario R F, Prabhakar S (2006) Lipids and diabetic nephropathy. Curr Diab Rep 6:455-462
50. Lassila M, Seah K K, Allen T J et al (2004) Accelerated nephropathy in diabetic apolipoprotein e-knockout mouse: role of advanced glycation end products. J Am Soc Nephrol
51. Dominguez J H, Tang N, Xu W et al (2000) Studies of renal injury III: lipid-induced nephropathy in type II diabetes. Kidney Int 57:92-104
52. Sandra, O., Song, K., Cai, W., Zheng, F., Uribarri, J., Vlassera, H. Insulin resistance and type 2 diabetes in high-fat-fed mice are linked to high glycotoxin intake (2005)
53. Hofmann, S M, Dong, H J, Li, Z, Cai, W, Altomonti, J, Thrung, S N, Zeng, F, Fisher, E A, Vlassera, H. Improved insulin sensitivity is associated with restricted intake of dietary glycoxidation products in the db/db mouse. Diabetes 51:2082-2089, 2002
54. Jia X, Olson D J, Ross A R, Wu L. Structural and functional changes in human insulin induced by methylglyoxal (2006) FASEB J 20:1555-1557.
55. Riboulet-Chavey A, Pierron A, Durand I, Murdaca J, Van Obberghen E. Methylgloxal impairs the insulin signaling pathways independently of the formation of intracellular reactive oxygen species (2006) Diabetes 55:1289-1299.

What is claimed:
1. A method for ameliorating or inhibiting insulin resistance in a subject, comprising administering to the subject an effective amount of a compound selected from the group consisting of LR-90 (methylene bis[4,4'-(2-chlorophenylure-idophenoxyisobutyric acid)]) and LR-102 (1,4-benzene-bis[4-methyleneaminophenoxyisobutyric acid]), or a pharmaceutically acceptable salt or derivative thereof.

2. The method of claim 1, wherein the subject is a mammal.

3. The method of claim 1, wherein the subject is a human.

4. The method of claim 1, wherein the subject has Type 2 diabetes or is in a prediabetic state.

5. A method for ameliorating or inhibiting insulin resistance in a subject, comprising administering to the subject a composition comprising an effective amount of a compound selected from the group consisting of LR-90 (methylene bis[4,4'-(2-chlorophenylureidophenoxyisobutyric acid)]) and LR-102 (1,4-benzene-bis[4-methyleneaminophenoxyisobutyric acid]) or a pharmaceutically acceptable salt or derivative thereof, and a pharmaceutically acceptable carrier or excipient.

6. A method for treating or slowing the development of Type 2 diabetes in a subject, comprising administering to the subject an effective amount of a compound selected from the group consisting of LR-90 (methylene bis[4,4'-(2-chlorophenylureidophenoxyisobutyric acid)]) and LR-102 (1,4-benzene-bis[4-methyleneaminophenoxyisobutyric acid]) or a pharmaceutically acceptable salt or derivative thereof.

7. The method of claim 6, wherein the administration provides benefits in FFA uptake, glucose uptake, glucose metabolism, insulin sensitivity, or reduction of Islet cell damage in the subject.

* * * * *

UNITED STATES PATENT AND TRADEMARK OFFICE
CERTIFICATE OF CORRECTION

PATENT NO. : 8,124,655 B2
APPLICATION NO. : 12/139822
DATED : February 28, 2012
INVENTOR(S) : Rahbar et al.

It is certified that error appears in the above-identified patent and that said Letters Patent is hereby corrected as shown below:

Col. 2, line 50: "d cell" should be -- β cell --

Col. 4, line 27: "lipidperoxidation" should be -- lipid peroxidation --

Col. 9, line 54: "TI" should be -- II --

Col. 13, line 9: "calorimetric" should be -- colorimetric --

Col. 20, line 22: "(Suppl" should be -- (Suppl 1):26-34 --

Col. 20, line 48: "Int" should be -- Int 58:2341-2350 --

Col. 20, line 58: "Schafer" should be -- Schäfer --

Col. 21, line 7: "Biophys" should be -- Biophys 48:147-157 --

Col. 21, line 42: "TI" should be -- II --

Col. 22, line 10: "Nov" should be -- Nov 277:44187-44194 --

Col. 22, line 40: "Nephrol" should be -- Nephrol 15:2125-2138 --

Signed and Sealed this
Twentieth Day of November, 2012

David J. Kappos
*Director of the United States Patent and Trademark Office*